(12) United States Patent
Liu et al.

(10) Patent No.: US 7,879,611 B2
(45) Date of Patent: *Feb. 1, 2011

(54) SYSTEM FOR FUNCTIONAL GENE DISCOVERY IN PLANTS

(75) Inventors: Alex Liu, Eugene, OR (US); George Wadsworth, Portland, OR (US); Helena Mathews, Portland, OR (US); Ry Wagner, Eugene, OR (US); Jill Van Winkle, Portland, OR (US); Sandra Peters, Portland, OR (US); Stephanie Clendennen, Portland, OR (US)

(73) Assignee: Agrigenetics Inc, Indianapolis, IN (US)

( * ) Notice: Subject to any disclaimer, the term of this patent is extended or adjusted under 35 U.S.C. 154(b) by 741 days.

This patent is subject to a terminal disclaimer.

(21) Appl. No.: 11/779,036

(22) Filed: Jul. 17, 2007

(65) Prior Publication Data

US 2007/0277265 A1    Nov. 29, 2007

Related U.S. Application Data

(63) Continuation of application No. 09/846,758, filed on May 1, 2001, now Pat. No. 7,250,553.

(60) Provisional application No. 60/201,245, filed on May 1, 2000.

(51) Int. Cl.
*C12N 15/82* (2006.01)

(52) U.S. Cl. ...................................... 435/468

(58) Field of Classification Search ........................ None
See application file for complete search history.

(56) References Cited

U.S. PATENT DOCUMENTS

| | | | |
|---|---|---|---|
| 5,664,402 A | 9/1997 | Sandvik et al. | |
| 5,770,786 A | 6/1998 | Sijmons | |
| 6,150,158 A | 11/2000 | Bhide et al. | |
| 6,194,638 B1 | 2/2001 | Dhugga et al. | |
| 6,300,542 B1 | 10/2001 | Briggs et al. | |
| 6,455,758 B1 | 9/2002 | Johnson | |
| 6,534,313 B1 | 3/2003 | Neff et al. | |
| 2002/0157130 A1 | 10/2002 | Wagner et al. | |

FOREIGN PATENT DOCUMENTS

| AU | 9516254 A | 10/1995 |
|---|---|---|
| WO | WO 01/09711 | 2/2001 |

OTHER PUBLICATIONS

Speulman et al. The Plant Cell. (Oct. 1999) vol. 11, pp. 1853-1866.
Tissier et al. The Plant Cell. (Oct. 1999) vol. 11, pp. 1841-1852.
Dey et al. "Further characterization and expression analysis of mirabilis mosaic caulimovirus (MMV) full length transcript promoter with single and double enhancer domains in transgenic plants," *Transgenics* 3(1): 61-70 (1999).
Usmanov, P.D. Aging of *Arabidopsis thaliana* seeds and its overcoming. Fiziolgiya Rastenii. (May 1999) 46 (3): 492-494.
"Large Scale sequencing of T-DNA insertion sites in *Arabidopsis thaliana*," Internet, 'Online! XP002185440 Retrieved from the Internet: <URL:http://www.szbk.u-szeged.hu/[arabidop/>, pp. 1-6.
Nottingham *Arabidopsis* Stock Centre—NASC: Internet, 'Online! XP002185441 Retrieved from the Internet: <URL:http://seeds.nottingham.ac.uk/Nasc/action.lasso?-token.user=10112587023&-response=browse/weigel/about_weigel.lasso&-nothing>, pp. 1-8.
"*Arabidopsis* Genome Initiative-AGI" Internet, 'Online! XP002185442 Retrieved from the Internet: <URL:http://www.arabidopsis.org/agi.html>, pp. 1-2.
Weigel et al. "Activation tegging in *Arabidopsis*," *Plant Physiology* 222(4): 1003-1013 (2000).
Wilson et al. "A dissociation insertion causes a semidominant mutation that increases expression of TINY, an *Arabidopsis* gene related to APETALA2" *Plant Cell, American Society of Plant Physiologists* 8(4); 659-671 (1996).
Terryn et al. "Plant Genomics," *GEBS Letters* 452(1-2): 3-6 (1999).
Szabados et al. "Identification of T-DNA insertions in *Arabidopsis* genes: the first *Arabidopsis* genome project in Hungary," *ISPMB Conference, 6th International Congress of Plant Molecular Biology*, pp. S01-S83 (2000).
Bell et al. "The Medicago Genome Initiative: A model legume database," *Nucleic Acids Research* 29(1): 114-117 (2001).

*Primary Examiner*—Marjorie Moran
*Assistant Examiner*—Anna Skibinsky
(74) *Attorney, Agent, or Firm*—Donald R. Stuart; Klarquist Sparkman LLP; Jarett K. Abramson

(57) ABSTRACT

The invention is directed to a method of multigenerational analysis of plants modified by insertional mutagenesis, and a method for associating plant mutant trait and genotype information. The invention is further directed to a method for managing data pertaining to plant mutant trait and genotype information in a database. The invention is further directed to a system for managing plant mutant trait and genotype information in a database, a system for allowing users to associate plant trait and genotype information, a system for facilitating business transactions with a user regarding plant materials or a gene sequence of interest to user and a computer-readable medium embodying a program of instructions for execution by a computer for implementing a system for allowing users to associate plant trait and genotype information.

22 Claims, 4 Drawing Sheets

SYSTEM FOR FUNCTIONAL GENE DISCOVERY IN PLANTS

CROSS-REFERENCE TO RELATED APPLICATIONS

This is a continuation of co-pending U.S. application Ser. No. 09/846,758, filed May 1, 2001 and issuing as U.S. Pat. No. 7,250,553 on Jul. 31, 2007, which in turn claims the benefit of U.S. Provisional Application No. 60/201,245, filed May 1, 2000. Both applications are incorporated herein in their entirety.

FIELD OF THE INVENTION

The invention is concerned with methods and compositions for associating plant phenotype and genotype information of interest.

BACKGROUND OF THE INVENTION

Common methods of analyzing gene function involve either knocking out gene expression and corresponding gene function, or over-expressing a gene and looking for an associated phenotype.

Conventional mutagenesis techniques frequently result in the identification of loss-of-function mutants and associated gene mutations that interfere with native gene. However, eukaryotic genomes contain a significant number of functional genes that have redundant coding sequences and regulatory regions within the genome. In addition, such methods do not often result in the identification of genes where loss-of-function results in early lethality. Both of these categories may potentially be identified through a method that results in gain-of-function.

Gain-of-function mutants may result from multiple mutations in a coding sequence that effect constitutive activation of the resulting protein, or by mutations that alter the level or pattern of gene expression. The latter type of mutations may be the result of altered promoter function in terms of the level of expression, for example, a constitutive versus inducible promoter, tissue or developmental stage specificity of a promoter or other regulatory element or enhanced native promoter activity.

Activation tagging is a method by which genes are randomly and strongly upregulated on a genome-wide scale, after which specific phenotypes can be screened for and selected. An activation T-DNA tagging construct was used to activate genes in tobacco cell culture allowing the cells to grow in the absence of plant growth hormones (Walden et al., *Plant Mol. Biol.* 26: 1521-8, 1994). A series of publications followed, including reports of genes isolated from plant genomic sequences flanking the T-DNA tag and putatively involved in plant growth hormone responses. (See, e.g., Miklashevichs et al., *Plant J.* 12: 489-98, 1997; Harling et al., *EMBO J.* 16: 5855-66, 1997; Walden et. al., *EMBO J.* 13: 4729-36, 1994 and Schell et al., *Trends Plant Sci.* 3: 130, 1998 which discusses investigation of a group of related studies.) In a similar study in Arabadopsis, a single gene was isolated from plant genomic DNA by plasmid rescue, identified and found to contain a gene, CKI1, which has been implicated in cytokinin responses in plants, the phenotype of which was confirmed when re-introduced into *Arabidopsis* (Kakimoto, *Science* 274: 982-5, 1996). In a more recent report, activation T-DNA tagging and screening plants for an early flowering phenotype led to the isolation of the FT gene (Kardailsky et al., *Science* 286: 1962-5, 1999).

Variations of the activation tagging technique include the use of the *Agrobacterium* gene 5 promoter (pg5), which is active only in proliferating cells and must insert directly adjacent to a plant gene in order to influence its expression, using, e.g., the nos promoter/hpt selection cassette (pCVHPT), originally described in Koncz et al., *Proc Natl Acad Sci USA* 86(21):8467-71, 1989. Another form of activation tagging utilizes a modified Ds transposon carrying the CaMV 35S promoter and a nos::hpt selection cassette (Wilson, et al., *Plant Cell* 8: 659-671, 1996). The modified Ds element is inserted into an antibiotic resistance cassette within a binary vector expression construct. Once introduced into *Arabidopsis*, the transposed Ds element (via the resident 35S promoter) is able to upregulate adjacent plant genes resulting in dominant gain-of-function mutations (Schaffer et al., *Cell* 93: 1219-1229, 1998; Wilson et al., 1996). Activation tagging vectors have been developed that are useful for screening tens of thousands of transformed plants for morphological phenotypes (Weigel D et al., *Plant Physiology,* 122:1003-1013, 2000).

These studies indicate the utility of such approaches to the identification of native genes which may then be evaluated for their function. Accordingly, generation of large amounts of data regarding plant genes and potential functions for the identified genes is possible. In order to make effective use of such information, the information must cataloged in a manner that makes it both searchable and accessible.

SUMMARY OF THE INVENTION

It is a general object of the invention to provide methods for correlating a mutant plant trait with the modified expression of one or more plant genes. It is a further general object of the invention to provide a system for managing data pertaining to plant identification numbers, mutant plant traits and plant genotype information in an electronic database.

The invention provides methods for the multigenerational analysis of plant traits, comprising plant transformation by insertional mutagenesis and selection and analysis of transformed T1 plants, followed by collection T2 seed and regeneration and further analysis of T2 plants or of subsequent progeny. Unique identification numbers are provided to represent each T1 plant in an electronic database. All data, particularly phenotypic and sequence data, pertaining to a T1 plant and to progeny plants subsequently generated from the parent plant, are recorded in the electronic database, which can associate data regarding a T1 plant with data regarding all generations of progeny plants generated from the parent T1 plant. The methods may be applied to *Arabidopsis*, tomato, rice, or other plants.

In one aspect of the invention, the insertional mutagen is an activation tagging vector. In some cases, the activation tagging vector comprises a multimerized enhancer element from the cauliflower mosaic virus (35S CaMV), a figwort mosaic virus (FMV) enhancer, a peanut chlorotic streak caulimovirus (PClSV) enhancer, or mirabilis mosaic virus (MMV) enhancer.

The invention provides methods for pooling and labeling T1 plants. The invention further provides methods for systematic data collection and recording, and for the transmission of data to the electronic database.

In one aspect the methods of the invention are used for analysis of morphological traits. In another aspect the methods are used in a directed screen to identify altered biochemical compositions, altered resistance to an herbicide, altered resistance to a plant pathogen, or altered stress tolerance.

The invention provides methods for generating a library of transformant seeds that may be accessed for various screens. In some cases, a directed screen may be performed using a subset of seeds in the library that are associated with a common mutant trait. In some cases, the library of seeds is of sufficient size to represent a mutation in essentially every gene in the genome.

The invention provides methods for associating a mutant trait with a candidate gene, for confirming the dominant inheritance pattern of a mutant trait, and for confirming the association of a dominant mutant trait with a candidate gene.

The invention also provides a system managing plant information for allowing a user to associate mutant trait information and genotype information. The system includes a database of records representing a library of plants having random genomic insertions of an insertional mutagen, where each record represents one plant and may contain mutant trait information for that plant and/or DNA sequence information representing one or more candidate plant genes responsible for one or more of the mutant traits. The system further includes a graphical user interface comprising a search engine capable of receiving a user-specified mutant trait or DNA sequence for searching the database, and a results display area for displaying one or more records identified by the search engine. The displayed information includes the identification number of a plant having the specified mutant trait or DNA sequence, and at least one of the following: (i) unsearched mutant traits associated with that plant, (ii) a visual representation of the plant, and (iii) DNA sequences representing candidate plant genes responsible for the searched mutant traits.

In a related aspect, the system managing plant information for allowing a user to associate mutant trait information and genotype information provides a system for facilitating business transactions with a user. The system includes a database of records representing a library of plants having random genomic insertions of an insertional mutagen, where each record represents one plant and may contain mutant trait information for that plant and/or DNA sequence information representing one or more candidate plant genes responsible for one or more of the mutant traits. The system further includes a graphical user interface comprising a search engine capable of receiving a user-specified mutant trait or DNA sequence for searching the database, and a results display area for displaying one or more records identified by the search engine. The displayed information further includes: (i) only unsearched mutant traits associated with the plant, (ii) unsearched mutant traits associated with the plant and a candidate gene sequence associated with one or more of the searched mutant traits of the plant, and (iii) unsearched mutant traits associated with the plant and a confirmed gene sequence responsible for one or more of the searched mutant traits of the plant, and an area for displaying a plurality of business arrangements available to a user. The business arrangements pertain to plant material or a plant gene sequence of a plant identified in the database, and the available business arrangements depend on the level of information in the particular record. In general, the plurality of business arrangements includes assignment, license and joint venture.

In another related aspect, the invention provides a computer-readable medium embodying a program of instructions for execution by a computer for implementing the system for allowing users to associate plant mutant trait and genotype information, such that the program of instructions imparts functionality to the executing computer, allowing the user to access and search the database to associate a searched mutant trait with a plant having other mutant traits of interest or with a plant having modified candidate gene sequences, or to associate searched DNA sequence information with a plant having phenotypic traits, and to view the results of the search.

BRIEF DESCRIPTION OF THE FIGURES

FIG. 1A depicts a pool of eight transformed T1 plants that have been transplanted into perimeter wells of a 9-well container. The central well contains a barcode from which T1 identification numbers are derived for each of the plants within the pool. FIG. 1B depicts a flat that can hold up to eight pools of plants.

DETAILED DESCRIPTION OF THE INVENTION

Figures 1A, 1B:
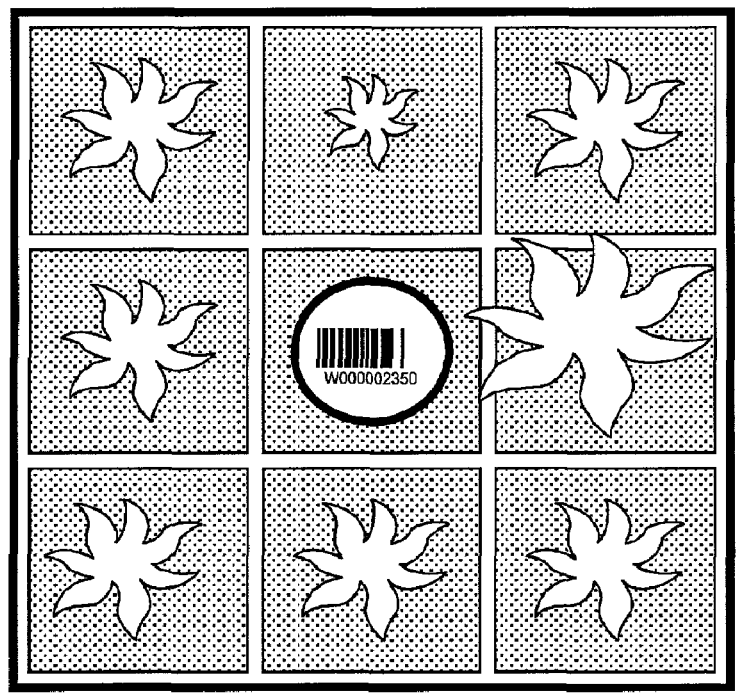
FIGS. 1A and 1B depict T1 plant organization and identification schemes.

I. Generating Plants with Modified Gene Expression Mutations by Insertional Mutagenesis The invention provides a system for functional gene discovery using a strategy based on modified expression of endogenous plant genes. More specifically, plants with modified genomes are produced, various phenotypic characteristics (traits) are observed or measured, and DNA analysis is used to associate plant phenotype and genotype information. As further described below, information regarding plant mutant traits and DNA sequences related to these traits are entered into an electronic database.

As used herein, a "mutant trait" and "mutant phenotype" are used interchangeably to refer to a characteristic of a plant that is modified as compared to a wild-type plant and that results from the interaction of the genetic make-up of the plant with the environment in which it develops. A mutant trait is identified by observation, analysis, and/or measurements (hereafter, observation and analysis are used interchangeably to encompass both observations by eye and particular analysis or measurements using particular conditions, techniques and/or equipment). Mutant traits include characteristics that improve the quality of a plant for a given purpose, such as for benefit to agricultural, food industry, ornamental plant, manufacturing, and/or pharmaceutical industries. The genomic alteration responsible for the mutant trait is referred to as the mutation.

II. Vectors for Generating Plants with Modified Gene Expression

The methods of this invention use insertional mutagenesis to modify gene expression. Insertional mutagenesis refers to modification of a plant genome by insertion of a foreign DNA element, termed an "insertional mutagen" into the genome. Generally, the insertional mutagen has been modified for experimental purposes.

The insertion of an insertional mutagen into a plant genome may produce a mutant trait in the plant bearing the insertion and in progeny plants bearing the insertion. Mutant traits may be dominant or recessive. For a given gene, dominant mutant traits are observed when a single allele has been mutated, whereas recessive mutant traits are observed only when all of alleles have been mutated. Dominant mutant traits are generally gain-of-function, i.e., resulting from molecular events (generally transcriptional, translational, or post-translational) that are not present in the wild type plant. Recessive mutant traits are generally loss-of-function, i.e., resulting from the loss of molecular events that are present in the wild type plant.

Gain-of-function mutations are readily produced by an insertional mutagen that comprises an enhancer element, followed by expression from the enhancer element. As used herein, "enhancer" and "enhancer element" are used interchangeably to refer to a nucleic acid sequence that functions to activate transcription of sequences from a nearby promoter. A promoter refers to a nucleic acid sequence that functions to direct transcription of downstream sequences. Sometimes, a promoter may function as an enhancer element. "Mis-expression" refers to ectopic transcription from plant host sequences that are proximal to an enhancer element. While mis-expression may lead to translation of a naturally occurring (i.e., wild type) protein, it may also generate synthetic RNA fragments that produce synthetic proteins, or that do not support any protein translation.

Loss-of-function mutations are readily produced by insertional mutagens that insert in genes, generally in the regulatory or coding sequences, and thereby disrupt the normal expression of that gene.

In preferred embodiments of the invention, insertional mutagens are used that can generate both loss-of-function and gain-of-function mutations.

In one preferred embodiment of the method described herein, the insertional mutagen is constructed in a manner that allows for conditional disruption of the enhancer element.

The methods of this invention include generating random insertions of the insertional mutagen. As used herein, "random" refers to non-targeted insertion. Preferably, the insertional mutagens used show minimal bias towards particular chromosomes or genes, positions along a chromosome, or particular regions of genes.

Methods for the construction of vectors for use in practicing the present invention are generally known to those of skill in the art. (See generally, Maniatis, et al., MOLECULAR CLONING: A LABORATORY MANUAL, 2d Edition (1989), and Ausubel, F E M., et al., Eds., CURRENT PROTOCOLS IN MOLECULAR BIOLOGY, John Wiley & Sons, Inc., Copyright (c)1987, 1988, 1989, 1990, 1993 by Current Protocols; Elvin, S. B., Schilperoort, R. A., Varma, D. P. S., eds. Plant Molecular Biology Manual (1990), all three of which are expressly incorporated by reference, herein).

Activation Tagging Vectors

Activation tagging ("ACTTAG") vectors provides exemplary mutagens for generating both loss-of-function and gain-of-function in plants.

Activation tagging is a process by which a heterologous nucleic acid construct comprising an enhancer element, is inserted into a plant genome. The enhancer element can act to enhance transcription of a single gene or may enhance transcription of two or more genes at the same time.

The "tag" is a region of the heterologous nucleic acid construct (i.e. the vector) which may be used to locate and thereby identify and characterize an introduced nucleic acid sequence that has integrated in the plant genome. Activation tagging nucleic acid constructs may be stably introduced into a plant genome in order to enhance expression of native (endogenous) plant genes. (See, e.g., Walden R, et al., *Plant Mol Biol* 26(5), 1521-8, 1994 Weigel D et al., 2000, supra)

In one approach, vectors for use in the methods of the functional gene discovery system of the invention contain regions of the T1 plasmid of *Agrobacterium tumifaciens*, which insert preferentially into potentially transcribed regions of the plant genome. The vectors further contain transcriptional enhancer sequences which activate gene expression at sites distant from the insertion point. An activation T-DNA tagging construct contains at a minimum a vector "backbone" suitable for amplification and maintenance of the construct in *E. coli* and *Agrobacterium*, and a T-DNA region. The T-DNA region, flanked by left and right *Agrobacterium* T-DNA borders, contains (1) an expression cassette for the selection of transformed lines containing the T-DNA insert; (2) sequences that facilitate the subsequent isolation or rescue of plant genomic sequences flanking the T-DNA insert; and (3) an enhancer region that positively influences the transcription of one or more plant genes flanking the T-DNA insertion. Appropriate vectors for use in the activation tagging approach to the functional gene discovery system are exemplified by the pSKI015 construct (GenBank Identifier [GI] 6537289; Weigel D et al., 2000, supra).

The key elements of pSKI015 are; (a) a pBstKS+ segment from the Bluescript™ plasmid, with an *E. coli* origin of replication (Stratagene), (b) the backbone from the RK2 plasmid, located between the left and right borders of the T-DNA, which contains the oriV and oriT regions responsible for stable replication in *Agrobacterium*; (c) a bialaphos resistance (BAR) gene encoding a phosphinothricin acetyltransferase enzyme; (d) a mannopine synthase (mas) promoter operatively linked to BAR gene, upstream thereof; (e) an octapine synthase (ocs) polyA termination element located downstream of the BAR gene, adjacent the left border of the plasmid, and (f) a multimerized (4×) CaMV 35S enhancer element. The pSKI015 construct contains the Bluescript pKS phagemid, which allows for isolation of plant genomic DNA flanking the T-DNA insert by plasmid rescue directly from plant genomic DNA and also provides the sole antibiotic selection marker (ampr) for selection and maintenance in the bacterial host in the presence of ampicillin or carbenicillin.

Enhancer Elements

A preferred insertional mutagen comprises an enhancer element. Preferred enhancer elements function in either orientation and function with a broad range of promoters. An exemplary enhancer element is the multimerized (4×) CaMV 35S enhancer, which is contained in the pSKI015 vector. Additional suitable enhancers include transcriptional enhancers from other caulimoviruses, such as the figwort mosaic virus (FMV), peanut chlorotic streak caulimovirus, (PClSV), and mirabilis mosaic virus (MMV). It has been found that tandem repeats of the enhancer regions of FMV, PClSV and MMV increase the expression of associated genes several-fold over single copies of the enhancer (Dey and Maiti, *Plant Mol. Biol.* 40: 771, 1999; Maiti and Shepherd, *Biochem. Biophys. Res. Commun.* 244: 440, 1998; Maiti et al., *Transgenic Res* 6:142-156, 1997). Maiti et al., 1997, describes an FMV sequence with strong promoter activity, which corresponds to positions 6691 to 7003 of the complete FMV genome sequence found at GenBank Accession No. X06166. The promoter for the full-length transcript (FLt) of PClSV is described in U.S. Pat. No. 5,850,019 and in Maiti et al., 1998, and corresponds to positions 5852 to 6101 of the complete genome sequence of PClSV (found at GenBank Accession No. U13988). MMV is a double-stranded DNA plant pararetrovirus belonging to the caulimovirus family. The complete genome sequence of MMV is unpublished. The sequence of the characterized MMV promoter fragment has been described by Dey et al., 1999. The fragment with the highest promoter activity extends from nucleotides −297 to +63 from the transcriptional start.

Selectable Markers

An insertional mutagen generally comprises a marker gene, which facilitates selection of transformants (i.e., plants or plant cells bearing genomic insertions of the insertional mutagen) and which encodes a selectable or screenable marker for use in plant cells. A selectable marker confers a trait that one can select for by chemical means, i.e., through the use of a selective agent (e.g., an herbicide, antibiotic, or the like). A screenable marker confers a trait identified through observation or testing. Numerous suitable marker genes known in the art may be employed in practicing the invention.

Exemplary selectable markers include but are not limited to antibiotic resistance genes, such as, kanamycin (nptII), G418, bleomycin, hygromycin, chloramphenicol, ampicillin, tetracycline, or the like. Additional selectable markers include a bar gene which codes for bialaphos resistance; a mutant EPSP synthase gene which encodes glyphosate resistance; a nitrilase gene which confers resistance to bromoxynil; a mutant acetolactate synthase gene (ALS) which confers imidazolinone or sulphonylurea resistance; or a methotrexate resistant DHFR gene.

In a preferred embodiment, the methods of the invention are carried out using a vector which includes the bar gene from *Streptomyces*, which encodes phosphinothricin acetyl transferase (PAT), that inactivates the active ingredient in the herbicide bialaphos, phosphinothricin (PPT). PPT inhibits glutamine synthetase, causing rapid accumulation of ammonia and cell death. Transgenic plants containing this gene exhibit tolerance to the herbicide, "BASTA". This gene can also be used as a selectable marker gene, since explants carrying the bar gene are capable of growing on selective media containing phosphinothricin (PPT), which is an active component of bialaphos.

In further embodiments, the methods of the invention are carried out using a vector which includes an herbicide resistance gene, conferring resistance to glyphosate-containing herbicides. Glyphosate refers to N-phosphonomethyl glycine, in either its acidic or anionic forms. Herbicides containing this active ingredient include "ROUNDUP" and "GLEAN". Exemplary genes for imparting glyphosate resistance include an EPSP synthase gene (5-enolpyruvyl-3-phosphosshikimate synthase) or an acetolactate synthase gene.

The particular marker gene employed is one that allows for selection of transformed cells as compared to cells lacking the DNA that has been introduced. Preferably, the selectable marker gene is one that facilitates selection at the tissue culture stage of the functional gene discovery system, e.g., a kanamyacin, hygromycin or ampicillin resistance gene.

The selection of an appropriate promoter effective to express the selectable marker-encoding sequence and the termination element for the selectable marker-encoding sequence may be accomplished by the use of well known, and/or commercially available sequences.

Transposon Sequences

As described above, exemplary insertional mutagens comprise T-DNA sequences. Alternative exemplary insertional mutagens comprise transposon sequences. Transposons, alternatively referred to as transposable elements, are naturally mobile pieces of DNA Exemplary transposons such as Ac, Ds, Mu and Spm are elements that can insert themselves into genes and cause mutations. The mutations may be unstable due to subsequent excision of the transposon from the mutant locus during plant or seed development. (See, e.g., Doring, H. P. and Starlinger *Ann. Rev. Genet.* 20:175-200, 1986; Federoff, N. "Maize Transposable Elements" in Mobile DNA. Wowe, M. M. and Berg, D. E., eds., *Amer. Soc. Microbiol., Wash., D.C., pp.* 377-411, 1989) An exemplary transposon-tagging strategy used to identify a semi-dominant mutation affecting plant height, hypocotyl elongation, and fertility has been described (see Wilson K et al., *Plant Cell* 8(4):659-71, 1996). Transposon sequences may be incorporated into an activation tagging nucleic acid construct in order to move an enhancer around the plant genome.

An enhancer trapping and a gene trapping system, based on the AciDs maize transposable elements, has been transferred into tomato, and found to be active. (See, e.g., Yoder, et al., *Mol. Gen. Genet.* 213:291-296, 1988.) In addition, methods for generating unlinked and stabilized transposition of Ds, and for selection of excision and reinsertion, where linked transposition events are most often recovered, have been described (See, e.g., Sundaresan, *Trends Plant Sci.* 1: 184-190, 1996; Meissner et al., *The Plant Journal* 12(6) 1465-1472, 1997).

III. Plants of the Invention

Plants of the invention have the following properties; (1) the ability to generate large numbers of transformants; and (2) traits or phenotypes which are observable or measurable. The methods of the invention are generally applicable to all species of *Arabidopsis*. Furthermore, the methods described herein are generally applicable to plants including, but not limited to species of *Arabidopsis, Lycopersicum* (tomato); Vitas (grape); *Fragaria* (strawberry); *Rubus* (raspberry, blackberry, loganberry); *Ribes* (currants and gooseberry); *Vaccinium* (blueberry, bilberry, whortleberry, cranberry); *Malus* (apple); *Pyrus* (pear); *Cucumis* sp. (melons); most members of the *Prunus genera*, sapota, mango, avocado, apricot, peaches, cherries, plums, nectarines; corn, rice, wheat, barley and other cereal grains; soybean, canola, sunflower and other oilseed crops; alfalfa, turfgrass and other forage crops.

Plant Transformation

Effective introduction of insertional mutagens which modify plant gene expression is an important aspect of the invention. It is preferred that the vector sequences be stably integrated into the host genome. Exemplary methods for introducing vectors into plant cells in the functional gene discovery system are *Agrobacterium*-mediated transformation, electroporation, microinjection, and microprojectile bombardment.

In one preferred embodiment, plant cells are transformed by infection with *Agrobacterium tumefaciens*. As will be appreciated, the optimal transformation method and tissue for transformation will vary depending upon the type of plant being transformed. Methods for *Agrobacterium*-mediated transformation are well known in the art.

The optimal procedure for transformation of plants with *Agrobacterium vectors*, will vary with the type of plant being transformed. Exemplary methods for *Agrobacterium*-mediated transformation include transformation of explants of hypocotyl, shoot tip, stem or leaf tissue, derived from sterile seedlings and/or plantlets. Such transformed plants may be reproduced sexually, or by cell or tissue culture.

*Agrobacterium* transformation has been previously described for a large number of different types of plants. See, for example, Bio/Technology 5:481-485, 1995 (banana); Ranier et al., *Bio/Technology* 8:33-38, 1990 (rice); McCormick et al., *Plant Cell Reports* 5:81-84, 1986 (tomato), Van Eck J M, et al., *Plant Cell Reports* 14: 299-304, 1995 (tomato); Norelli et al., *HortScience,* 31:1026-1027, 1996 (apple); Miguel C M et al., *Plant Cell Reports* 18: 387-93, 1999 (almond); Cabrera-Ponce J L et al., *Plant Cell Reports* 16: 255-260, 1997, Delbreil B et al., *Plant Cell Reports* 12:129-132, 1993 (asparagus); Mogilner N et al., *Mol Plant Microbe Interact* 6(5):673-5, 1993 (avocado); Hosoki T et al., *J. Japan Soc. Hort. Sci.* 60: 71-75, 1991 (broccoli); Hardegger M et al., *Molecular Breeding* 4: 119-127, 1998 (carrot); Bhalla P L and Smith N, Molecular Breeding 4: 531-41, 1998 (cauliflower); Catlin D et al., *Plant Cell Reports* 7: 100-103, 1988 (celery); Sarmento G G et al., *Plant Cell Tissue and Organ Culture* 31: 185-193, 1992 and Trulson A J et al., *Theor Appl Genet* 73: 11-15, 1986 (cucumber); Scorza R et al., *Plant Cell Reports* 14: 589-92, 1995 and Franks T et al., *Molecular Breeding* 4:321-33, 1998 (grape); Nakamura Y et al., *Plant Cell Reports* 17:435-440 (persimmon); Zhang H X and Zeevaart J A D, *Plant Cell Reports* 18: 640-45, 1999 (spinach); U.S. Pat. Nos. 5,750,871 and 5,463,174 (transformation of *Brassica* species using hypocotyl tissue); and U.S. Pat. Nos. 5,824,877 and 5,569,834 (soybean transformation which requires removal of the hypocotyl tissue).

IV. Methods for Multigenerational Plant Trait Analysis

The methods of this invention comprise generation of transformed plants with modified gene expression and the multigenerational analysis of transformed plants. As used herein, the term "T0" refers to the generation of plant tissue that is subjected to transformation. The term "T1" refers to the generation of plants that are derived from the seed of T0 plants and in which transformed plants can first be selected by application of a selection agent, e.g., an antibiotic or herbicide, for which the transgenic plant contains the corresponding resistance gene. The term "T2" refers to the generation of plants by self-fertilization of the flowers of T1 plants, previously selected as being transgenic.

In practicing the method, a large number of T0 plants or plant cells are transformed by generating random genomic insertions of an insertional mutagen, such that the marker gene encoded by the insertional mutagen is expressed. Plant cells are generally selected by their ability to grow in the presence of an amount of selective agent that is toxic to non-transformed plant cells, then regenerated to yield mature plants.

The selection of plants transformed with the insertional mutagen is commonly performed in soil, but plants can also be selected on solid medium.

Each transformed T1 plant is assigned an identification number that is recorded in an electronic database. Transformed plants are typically observed for phenotypic variations (i.e., mutant traits) relative to wild-type plants of the same species, which are also recorded in the database. In a preferred embodiment of the invention, plants are observed in pools. In a further embodiment, each group or pool of plants is identified by a bar code, such that individual plants within the group also have a unique identifier. In one exemplary embodiment, there are 8 plants per pool and 8 pools per flat of plants wherein each pool and flat have a unique identifier. In addition, individual plants may be identified by location within the pool and flat (FIGS. 1A and 1B). More specifically, transformed plants are transplanted into perimeter wells of a multiwell container comprising a central well in which a barcode is provided. Each perimeter well contains a single T1 plant, and the identification number assigned to each T1 plant derives from the barcode in the corresponding central well and the relative position of the perimeter well holding said T1 plant. The relative position refers to the position of a plant in a perimeter well that is uniquely identified with respect to the position of other plants within the pool. FIG. 1, for instance, depicts a system wherein the well in the top left corner of a pool is assigned a position 1, and, moving clockwise around the pool, subsequent wells are assigned positions 2-8.

In one exemplary approach, T1 plants are observed closely on a regular basis, e.g., twice monthly, with observations entered into a notebook and/or observations and/or measurements recorded using a hand-held electronic data entry device (e.g., a Palm Pilot) equipped with a barcode scanner, followed by downloading of the computer records for the observations and measurements into a computer database. Bulk or individual leaf tissue may be collected from T1 plants. Observations may also be documented by photography of pools and interesting individual plants using a digital camera. Identification of mutant traits may also take place in the T2 generation and is further described below.

A fraction of the plants in which the expression of native genes is modified will exhibit a visually detectable mutant trait.

Figure 2:
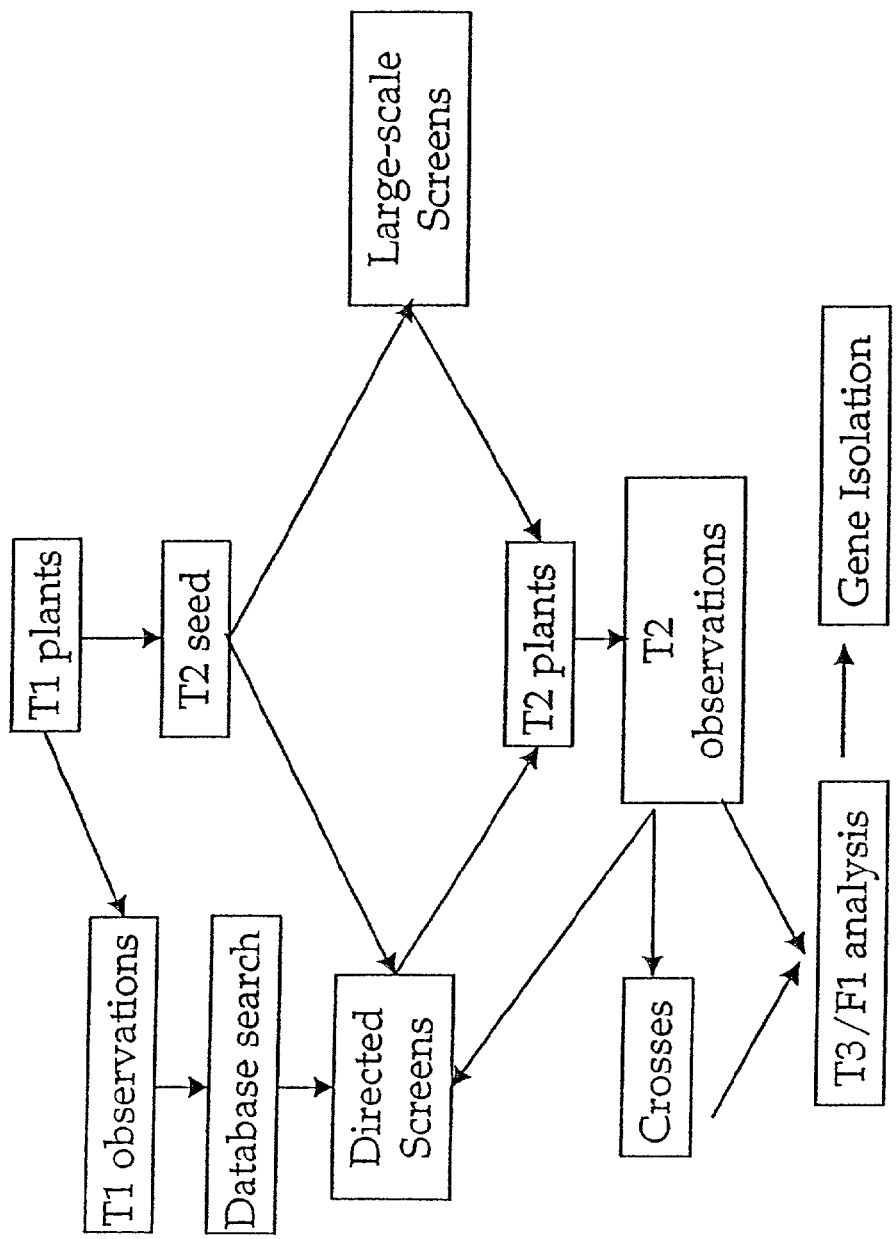
FIG. 2 is a flow chart that depicts various features of multigenerational plant trait analysis.

In practicing the invention, T2 seed is collected from T1 plants, which have survived selection, and sown to yield T2 plants. Bulk or individual leaf tissue may be collected from T2 plants (and stored at −80° C.), and further analysis may be done on whole plants or plant tissues. In general, T2 plants that display mutant traits are also grown until they produce seed; T3 seed is collected and sown to yield T3 plants. Similar to the treatment of T2 plants, T3 plants are observed, observations recorded, and tissue collected. This cycle may be repeated multiple times. Various features of multigenerational plant trait analysis are depicted in FIG. 2. Exemplary phenotypic analysis methods are further described below.

Molecular analysis of the plants, particularly those that exhibit mutant traits, is performed in parallel to or following phenotypic analysis. In a preferred embodiment, the plants are further analyzed by means such as PCR and/or Southern hybridization to verify genomic integration of the insertional mutagen, and the plant genomic DNA flanking the insertion site of the insertional mutagen is isolated and characterized. Further aspects of molecular analysis, including identification of the gene responsible for a mutant trait, are further described below.

Detecting, Selecting and Characterizing Transformants

The invention provides methods for the systematic evaluation of mutant traits, which generally takes place in the T1 or T2 generation but may also take place in subsequent generations. Exemplary phenotypic evaluations include, but are not limited to morphology, biochemical analysis, herbicide tolerance testing, herbicide target identification, fungal resistance testing, bacterial resistance testing, insect resistance testing, and screening for increased drought, salt and metal tolerance.

As set forth above, plants are observed closely by eye on a regular basis, e.g., twice monthly, for morphological traits, with observations entered into a notebook and/or recorded using a hand-held electronic data entry device. Whole plants or plants tissues may also be analyzed for altered biochemical composition and pathogen, stress, and herbicide resistance. The invention provides methods for tracking and managing data from analysis of mutant traits. Data from all analyses of mutant traits are entered into an electronic database and linked to the specific identification number for the plant or group of plants tested. In one embodiment, data collected with hand-held electronic data entry devices are automatically downloaded into the electronic database.

Screening Methods

Screens for Morphological Traits

Morphological traits are those traits that are observed by eye, with or without aid of a magnification device, under normal growth conditions. Exemplary morphological traits include leaf number, leaf pigmentation, leaf shape, seed number, pattern or distribution of leaves or flowers, flower size, flower number, time of flowering (early or late), flower pigmentation, flower shape, dwarf or giant stature, stem length between nodes, root mass and root development characteristics. An important aspect of the invention is the consistent descriptions of mutant traits that are entered into the database, in order to facilitate data recovery when searching the database containing mutant trait information. To this end, a predefined vocabulary of terms is generated to describe classes of mutant trait. Exemplary terms (i.e., abbreviations) from a predefined vocabulary pertaining to morphological traits are provided below in Table 1.

TABLE 1

Morphological Phenotypes And Abbreviations Therefor.

| Areas of variation | Abbreviations | Indications |
| --- | --- | --- |
| leaf petiole | LEP | absence of, short, or long petioles of rosette leaves |
| leaf margin | LEM | variations in leaf margin |
| leaf epidermis | LEE | variations in cuticle: texture, waxiness, etc of leaf surface |
| leaf lamina | LEL | variations in laminar length, width |
| trichome | TRI | variations in number, shape or location of trichomes |
| stem elongation | SEL | spindly; increased/decreased internodes |
| shoot meristem | STM | absence, multiple, or other abnormality in shoot meristems |
| apical dominance | APD | variation in meristem dominance, release of axials |
| meristem fate | MFA | variations in organs formed by meristems: leaves, determinant infloresences |
| pigment | PIG | overproduction of accessory pigments (anthocyanins primarily) |
| chlorophyll | CHL | yellowing or deeper greening in leaves |
| sterility/fertility | STE | no/abnormal silique development, no viable seed |
| fruit development | FRD | abnormal silique development: early/late dehiscion, not bicarpellate, etc |
| floral organ | FLO | variation in number, placement and shape of floral parts |
| early flowering | ELF | precocious relative to surrounding plants; <9 leaves, bolt >0.5 cm. |
| late flowering | LAF | bolts lag relative to surrounding plants; >12 leaves, bolt <0.5 cm. |
| dwarf | DWF | all plant parts reduced-proportional |
| giant | GIA | all plant parts enlarged-proportional |

Directed Screens

In one aspect of the invention a directed screen is used to analyze mutant traits. By "directed screen" is meant the employment of particular equipment, analytical techniques, and/or conditions to identify a single type of mutant trait or class of mutant traits. Exemplary directed screens analyze changes in the biochemical composition of plant tissues, and in resistance to pathogens, herbicides, and stress.

A directed screen to identify a particular mutant trait may be performed without regard to any other mutant traits displayed by the plants analyzed. Sometimes, however, it may be advantageous to analyze a particular class of plants displaying mutant traits. For instance, we have found that in screens for drought-resistance and for fungal resistance, transformant plants displaying morphological phenotypes are more likely than morphologically normal transformant plants to display drought- or fungal-resistance. When a directed screen is performed on a particular class of transformant plants, the database is queried in order to determine, by identification number, which transformant plant lines have a particular mutant trait of interest.

A. Biochemical Analyses

Exemplary metabolic characteristics of interest include altered biochemical composition of leaves, seeds, fruits and roots and flowers and seedlings which result in a change in the level of vitamins, minerals, oils, elements, amino acids, carbohydrates, lipids, nitrogenous bases, isoprenoids, phenylpropanoids or alkaloids.

More specifically, exemplary metabolic characteristics of interest include altered biochemical composition of vegetative (e.g. leaves, stems, roots) and reproductive tissues (e.g. seeds, fruits, and flowers) which result in a change in the level of vitamins, minerals, oils, elements, amino acids, carbohydrates, polymers, lipids, waxes, nitrogenous bases, isoprenoids, phenylpropanoids or alkaloids. Exemplary metabolic characteristics of interest may also include the relative abundance of various metabolite classes (e.g. high protein, low carbohydrate), and quantitative physiological descriptors such as Harvest Index, Fresh Weight/Dry Weight Ratio, seed mass, and seed density.

The skilled artisan will recognize that a variety of techniques exist for analyzing these metabolites both individually, and in mixtures. Appropriate general techniques may include but are not limited to, enzymatic methods, chromatography (high-performance liquid chromatography HPLC, gas-chromatography GC, thin layer chromatography) electrophoresis (e.g. capillary, PAGE, activity gels), spectroscopy (e.g. UV-Visible, Mass-spectroscopy MS, Infrared and Near-Infrared IR/NIR, Atomic Absorption AA, Nuclear Magnetic Resonance NMR), and hybrid methodologies (e.g. HPLC-MS, GC-MS, CE-MS).

The essential elements of a useful methodology are the ability to generate quantitative results and the ability to perform rapid, automated analysis. Some selected examples of specific methodologies are listed here but the skilled artisan will recognize that many existing methods can be further optimized for speed and automation. Commercially available chemical analysis software can be used for the accumulation and interpretation of chemical data and the derived results can be exported to a database where correlations may be examined between metabolic changes and other observed phenotypes. One example of such a chemical analysis software package is Waters Millennium Software (Waters Corp., Millford, Mass.). An example of a method for the analysis of lipid components is that of Browse et al. (*Biochem. J.* 235:25-31, 1986). Taungbodhitham and colleagues (*Food Chemistry* 63, 4:577-584, 1998) optimized a method for the extraction and analysis of carotenoids from fruits and vegetables. Other investigators have reported analysis conditions for the simultaneous analysis of a variety of pigment components from plant tissues (Barua and Olsen, *Journal of Chromatography* 707:69-79, 1998; Siefermann-Harms, *J. of Chromatography* 448:411-416, 1988). General seed compositional analyses are described in a number of references (e.g. Approved Methods of the American Association of Cereal Chemists 10$^{th}$ Edition, 2000, ISBN 1-891127-12-8, American Assoc. of Cereal Chem.) Focks and Benning describe a method for screening for seed density and seed composition (*Plant Physiol.* 118: 91-101, 1998). These methods are by no means exhaustive, but rather, are presented to suggest the wealth of available methodologies available to the skilled artisan for analysis of chemical constituents.

B. Herbicide Tolerance/Targets

The control of weeds is of economic importance to optimal production and quantity of fruits, seeds, foliage and flowers. A directed screen to identify altered resistance to an herbicide can identify both gene targets for herbicides (which are useful for the development of novel herbicidal compounds) and plant genes that can be altered to yield plants with increased resistance (tolerance) to herbicides. Assays for herbicide activity/resistance include petri-dish assays, soil assays and whole-plant assays. Exemplary endpoints indicative of herbicidal activity include inhibition of seed germination; stunting of shoots; development of abnormal seedlings that do not emerge from soil; inhibition of main and lateral roots; late emergence; newer leaf tissue that is yellow (chlorotic) or brown (necrotic); leaf tissue that lacks proper pigmentation; malformation or necrosis of terminal meristematic areas; stem twisting and epinasty; early petioles that turn down; abnormal growth responses, e.g. abnormal leaf, flower or seed formation; and rough or crumbly leaves.

Weed targets of interest include, but are not limited to, Wild Oat, Green Foxtail, Chickweed, Cleavers, Kochia, Lamb's Quarters, Canola, Leafy Spurge, Canada Thistle, Field Bindweed And Russian Knapweed, Crabgrass, Goosegrass, Annual Bluegrass, Common Chickweed, Smartweed, Wild Buckwheat, Henbit, Lawn Burweed, Corn Speedwell, Alfalfa, Clover, Dandelion, Dock, Dollarweed, Woodsorrel, Betony, Daisy, Shepherd's-Purse, Thistles, Knapweeds, Vetch, Violets, Yarrow and Wild Mustard.

C. Plant Pathogen Resistance Testing

The control of infection by plant pathogens is of significant economic importance, given that pathogenic infection of plants (more specifically, infection of seeds, fruits, blossoms, foliage, stems, tubers, roots, etc.) can inhibit production of fruits, seeds, foliage and flowers, in addition to causing a reduction in the quality and quantity of the harvested crop.

In general, most crops are treated with agricultural anti-fungal, anti-bacterial agents and/or pesticidal agents. However, damage due to infection by pathogens still results in revenue losses to the agricultural industry on a regular basis. Furthermore, many of the agents used to control such infection or infestation cause adverse side effects to the plant and/or to the environment.

Plants with enhanced resistance to infection by pathogens would decrease or eliminate the need for application of chemical anti-fungal, anti-bacterial and/or pesticidal agents.

For a discussion of the value of identifying insect resistance loci in plants, see Yencho G C et al., *Annu Rev Entomol.*, 45:393-422, 2000.

i. Fungal Resistance

An exemplary screen for fungal resistance includes testing for resistance to infection by the following fungal pathogens: (1) *Albugo candida* (white blister), (2) *Alternaria* brassicicola (leafspot), (3) *Botrytis cinerea* (gray mold), (4) *Erysiphe cichoracearum* (powdery mildew), (5) *Peronospora* parasitica (downy mildew), (6) *Fusarium oxysporum* (vascular wilt), (7) *Plasmodiophora brassicae* (clubroot), (8) *Rhizoctonia solani* (root rot), (9) *Pythium* spp. (damping off), (10) *Colletotrichum coccode* (anthracnose), and (11) *Phytopohthora infestans* (late blight). Plants are susceptible to attack by a variety of additional fungi, including, but not limited to species of *Sclerotinia, Aspergillus, Penicillium, Ustilago*, and *Tilletia*.

ii. Bacterial Resistance

Exemplary screens for bacterial resistance include testing for resistance to infection by the following bacterial pathogens: (1) *Agrobacterium tumefaciens* (crown gall); (2) *Erwinia* tracheiphila (cucumber wilt); (3) *Erwinia stewartii* (corn wilt); (4) *Xanthomonas* phaseoli (common blight of beans); (5) *Erwinia amylovora* (fireblight); (6) *Erwinia* carotovora (soft rot of vegetables); (7) *Pseudomonas syringae* (bacterial canker); (8) *Pelargonium spp, Pseudomonas cichorii* (black leaf spot); (9) Xanthomonasfragariae (angular leaf spot of strawberry); (10) *Pseudomonas syringae* (angular leaf spot of cucumber, gherkin, muskmelon, pumpkin, squash, vegetable marrow, and watermelon); (11) *Pseudomonas syringae* and *Pseudomonas morsprunorum* (bacterial canker of stone fruit); (12) *Xanthomonas campestris* (bacterial spot, bacteriosis, shot hole, or black spot of peach, nectarine, prune, plum, apricot. cherry or almond).

Important components of an exemplary bacterial disease screen are, (a) assaying plants that have a mature rosette with fully expanded leaves-fully expanded leaves are more amenable to symptom-based evaluation than leaves which have not fully expanded; (b) assaying plants for which flowering has not initiated; and (c) physical placement of each plant under evaluation in a manner that allows for easy scoring of symptoms (resistant vs. susceptible phenotype) and recording of results, e.g., digital imaging of each individual plant. Transplanting of seedlings to individual cells fulfills these spatial requirements. An exemplary bacterial resistance screen is further described in Example 4.

iii. Viral Resistance

Attempts to control or prevent infection of a crop by a plant virus have been made, yet viral pathogens continue to be a significant problem in agriculture. Approaches to viral resistance include targeting (1) establishment of infection, (2) virus multiplication, and/or (3) viral movement.

Exemplary references relative to viral pathogen resistance in *Arabidopsis* include references directed to: turnip mosaic potyvirus (Martin, A. M., et al., *MPMI* 12: 1016-1021, 1999); turnip crinkle virus (Simon, A. E et al., *MPMI* 5, pp. 496-503, 1992; A. E. Simon et al., In: ARABIDOPSIS THALIANA AS A MODEL FOR PLANT PATHOGEN INTERACTIONS, K. R. Davis and R. Hammerschmidt (Eds), 1993, APS Press, St. Paul, Minn.; Li, X H and Simon, A E *Phytopathology*, 80 (3) pp. 238-242, 1990; Dempsey D. A et al., *Phytopathology* 83:1021-1029, 1993); cauliflower mosaic virus (Leisner, S M and Howell, S H, *Phytopathology*, 82: 1042-1046, 1992; Callaway, A et al., *MPMI* 9:810-818, 1996); geminivirus infection (Lee, S et al., Plant J. 6:525-535, 1994); tobacco ringspot nepovirus (Lee, J et al., *MPMI*, 9:729-735, 1996); tobamoviruses (Lartney, R T et al., *MPMI* 11:706-709, 1998); tobacco etch virus (Mahajan, S K et al., *Plant J.* 14:177-186, 1998); oilseed rape mosaic tobamovirus (Martin A et al., *Aust. J. Plant Physiol.* 24:275-281, 1997); and cucumber mosaic virus (Takahashi, H et al., *Plant J.* 6:369-377, 1994; Yoshii, M et al., *J. Virol.* 72:8731-8737, 1998).

An exemplary screen for virus resistance includes testing for resistance to infection by the following viral pathogens: plum pox potyvirus (PPV), which affects stone fruit trees (Lopez-Moya J J et al., *J Biotechnol* 76(2-3):121-36, 2000); tobamovirus (Bendahmane M et al., *Adv Virus Res* 53:369-86, 1999); tobacco mosaic virus (Beachy R N, *Philos Trans R Soc Lond B Biol Sci* 354(1383):659-64, 1999; Erickson F L et al., *Philos Trans R Soc Lond B Biol Sci* 354(1383): 653-8, 1999; Buck R M Philos Trans R Soc Lond B *Biol Sci* 354(1383): 613-27, 1999); tospovirus (Prins M and Goldbach R, *Trends Microbiol* 6(1):31-5, 1998); potyviruses which mainly infect members of the Solanaceae family, including potato, tobacco, and tomato (e.g., U.S. Pat. No. 5,986,175); and testing for resistance to viral pathogens using coat protein-mediated protection (Miller E D and Hemenway C, *Methods Mol Biol* 81:25-38, 1998; Malpica C A, *Subcell Biochem* 29:287-320, 1998).

iv. Insect/Nematode Resistance

In general, most crops are treated with chemical pesticides and insecticides have been effective in controlling many harmful insects. However, damage due to insect infestation remains a problem and results in revenue losses to the agricultural industry on a regular basis. In addition, many insecticides are expensive; they require repeated applications for effective control and cause adverse side effects to the plant and/or the environment. Further, there are concerns that insects have or will become resistant to many of the chemicals used in controlling them. Plants with enhanced insect resistance would decrease or eliminate the need for application of such chemical pesticides.

Exemplary screens for plant resistance to insects include assays that target insect species of the orders Lepidoptera, Hemiptera, Orthoptera, Coleoptera, Psocoptera, Isoptera, Thysanoptera and Homoptera. In general such assays are used to detect the actual killing of insects, the interruption of insect growth and development so that maturation is slowed or prevented (e.g., anti-feedant activity), and/or the prevention of ovaposition or hatching of insect eggs.

References relevant to insect resistance in *Arabidopsis* include: Mitchell-Olds, T, *Novartis Found Symp* 223:239-248, discussion 248-52, 1999; Santos, M O et al., MOLECULAR BREEDING: NEW STRATEGIES IN PLANT IMPROVEMENT, Boston Kluwer Academic Publishers, 3:183-194, c1995; and McConn, M et al., *Proc. Natl. Acad. Sci. U.S. A.* 94 (10) 5473-5477, 1997.

An exemplary screening assay for insect resistance involves testing for susceptibility to attack by a variety of insect species that attack different parts of the plant, for example the stem, the leaves and the roots.

Since it expected that many resistance mutations will be loss-of function (recessive) it is important that enough transformed plants (which have survived application of the selective agent) are evaluated to insure that a homozygous mutant is tested. Each individual surviving plant is tested separately and if insect/nematode resistance is detected, the individual plant is retained for seed collection. For each test, the interaction of the insects or nematodes with a mutant plant is compared to the interaction of the same species of insect or nematode with wild type plants.

A representative insect that feeds on the stems of *Arabidopsis* plants is *Myzus persicae* (aphid). In an exemplary assay, *Arabidopsis* plants of any size, but preferably at least three weeks old, are infested with a mixed population of *Myzus persicae* and then held in a controlled environment at approximately 75° F. Each test plant is individually monitored for development of the aphid population for up to seven days. If a plant is identified where the aphid population is lacking or reduced relative to the population on the wild type plants, the plant is immediately reinfested for confirmation. If confirmed, the individual plant(s) are retained for seed collection.

A representative insect that feeds on the leaves of *Arabidopsis* plants is *Plutella xylostella*. In an exemplary assay, *Arabidopsis* plants with rosette leaves of sufficient size to collect leaf tissue, typically, but not limited to, a disc 3-7 mm in diameter, are used. Leaf pieces to be tested are placed in a plastic dish, larvae or eggs of *Putella xylostella* are added to the dish and the dish is covered. Feeding consumption is monitored until tissue in the wild type test is consumed, with failure of the larvae to consume any of the leaf pieces from a mutant *Arabidopsis* plant indicative of potential resistance. If a leaf piece is not consumed, then the test is repeated tracking each plant individually. If a reduction in feeding is confirmed, the individual plant(s) are retained for seed collection.

Nematode resistance is best assessed using either *Meloidogyne* species or *Heterodera* species. This test can be conducted either in agar or soil. In either case, shortly after germination of the plants, eggs or juveniles of the nematode species are added to the growing medium. The plants are then held long enough for wild type plants to show a response, typically plant death, root galling or cysts; which generally takes place in 3-10 weeks. Staining techniques may also be used to identify nematode damage. Plants that unexpectedly survive the nematode attack or plants that show no visible root galls, cysts or penetration are potentially resistant and are retained for seed collection.

D. Stress resistance

Crops are generally unable to withstand various stresses, including drought conditions, and conditions of high salt (reviewed in Sanders D, Current Biology 10: R486-488, 2000) or metals. Understanding the molecular basis for stress resistance is an active area of research. For instance, *Arabidopsis* metal response mutants such as cup1-1, cad1, cad2, and man1 (a manganese hyperaccumulator; Delhaize E, Plant Physiol 111:849-551, 1996) were discovered in screens for hypersensitivity or hyperaccumulation of metal ions. Other research performed to identify genes involved in response to metal is described in the following references: Degenhardt J et al., *Plant Physiol* 117:19-27, 1998; Larsen P B et al., *Plant Physiol* 110:743-51, 1996; Larsen P B et al., *Plant Physiol* 117:9-18, 1998.

Directed screens to identify altered stress resistance (e.g., to drought, salt, and metal) may identify genes that can be altered to yield plants with increased stress resistance (tolerance). Such discoveries may ultimately result in an ability to cultivate plants on a broader range of land, such as arid and/or saline land.

Directed screens performed to identify genes involved in stress response use laboratory conditions that simulate the particular stress, such as water deprivation, or high concentration of salt or metal in the media and/or soil. Methods for exemplary screens are provided in the Examples.

V. Gene Isolation and Analysis

An important aspect of the invention is the identification of genes responsible for mutant traits. As used herein, a "gene responsible for a mutant trait" is used to refer to a gene whose expression is modified by insertion mutagenesis, wherein this modification causes the mutant phenotype. In one aspect of gene identification, genomic DNA is recovered by isolating and sequencing DNA adjacent to the inserted insertional mutagen. If the pSKI015 vector is used, the right border sequence is generally analyzed first. Plasmid rescue (Behringer and Medford, *Plant Mol. Biol. Rep.* 10(2):190-198, 1992), inverse PCR (Novak, J and Novak, L, *Promega Notes Magazine Number* 61:27, 1997), and TAIL-PCR (Liu et al. *Plant Journal* 8(3) 457-463, 1995) techniques provide exemplary methods for recovery of DNA flanking an insertional mutagen. As used herein, "rescuing DNA" and "rescuing sequence(s)" are used interchangeably to refer to the recovery, isolation, and amplification of DNA flanking an insertional mutagen. Techniques such as genome walking may be used to identify further DNA sequences surrounding the insertional mutagen; reagents for genome walking are commercially available (e.g., GenomeWalker™ from Clontech, Palo Alto, Calif.). Following the recovery of flanking DNA, the sequence of rescued DNA is determined by standard DNA sequencing methods, and candidate gene(s) responsible for a mutant trait are identified from the rescued genomic sequence or from a DNA fragment encompassing, overlapping, or flanking the rescued sequence.

Methods for identifying candidate genes may vary, depending in part on the plant use. In general, rescued sequences are analyzed by determining homology to known sequences in databases (public/private) and/or full sequencing and/or analysis using sequence analysis software, as further described below. The presence of one or more open reading frames (ORFs) is determined. In general, predicted or confirmed ORFs within 5-10 kilobase (kb) of the inserted insertional mutagen comprise candidate genes and are further investigated for association with the mutant trait. In one example, sequences of from about 100 to 3000 base pairs flanking the insertion site are recovered by plasmid rescue. The rescued sequences are used to pull out longer native plant DNA sequences of from about 20 kb on each side of the insertion site and to construct cosmid clones containing from about 20 to 40 kb of the native plant DNA. The sequences in the cosmid clones are then screened for open reading frames, and used to probe Northern blots of total RNA or mRNA derived from a particular plant. Genes having altered expression in transformed plants relative to plants that have not been transformed are identified in this manner. (See, e.g., METHODS IN PLANT MOLECULAR BIOLOGY AND BIOTECHNOLOGY, Glick and Thompson Eds., CRC Press, pages 67-73 and 89-106, 1993). Methods for construction of cosmid clones are provided in chapter 3 of Maniatis, et al. (1989, supra). In another example, which is appropriate for *Arabidopsis* and may be applied to other plants with sequenced genomes, the rescued sequence is subjected to a basic BLASTN search using the sequence comparison program available at the ncbi.nlm.gov/BLAST website and to a search of the *Arabidopsis* Information Resource (TAIR) database at the *arabidopsis*.org website. A BAC or another clone containing the rescued sequence is identified and subjected to analysis by GENSCAN or another gene prediction program.

Computational Analysis

In general, computational analysis of sequence is an important part of the identification of candidate genes. Bioinformatics analysis may be used to identify and predict ORFs in sequence surrounding an insertion site and to investigate the potential function and genetic complexity of isolated ORFs.

In one approach, an identified genomic sequence (e.g., flanking an insertional mutagen) is used to do NCBI BLAST™ similarity search using the interface provided at the ncbi.nlm.nih.gov/BLAST/website. The BLAST search results indicate the presence or absence of related sequences that have been deposited in the public databases that are searched, as of the date of the search.

Computational analysis may be used for primer design, for instance for genome walking. In general, the largest rescued sequence is used to design new primers to sequence an extended genomic insertion. Such primers may be designed using a computer program, for example, the Primer3 program found at the genome.wi.mit.edu/cgi-bin/primer/primer3_www.cgi/website.

Several major sequence databases and sources of sequence information and analysis tools currently exist, many accessible through the internet. Interesting databases for bioinformatics analysis include the following:

The National Center for Biotechnology Information (NCBI, at the ncbi. nlm.nih.gov website) supports one of the premier sequence databases (GenBank) and sequence homology search algorithms (BLAST) as well as useful tools for gene structure analysis. Potential gene function by sequence homology with genes or proteins having known or putatively known functions may be determined using the Basic Local Alignment Search Tool (BLAST, available through the ncbi.nlm.nih.gov/blast/website). BLAST is used to compare gene and protein sequences against others in public databases, and is a useful method for assigning putative gene identification based on sequence similarity to previously characterized genes. BLAST 2.0 or "Gapped BLAST" (Alstchul et al., *Nucleic Acids Res.* 25:3389-3402, 1997), allows the user to input protein and nucleic acid sequences and compare them against a selection of NCBI databases, most frequently a non-redundant combination of entries in GenBank, EMBL, DDBJ and PDB sequences (but not EST, STS, GSS, or phase 0, 1 or 2 HTGS sequences, which are searched separately) at the nucleotide level, and all non-redundant GenBank CDS translations, PDB, SwissProt, PIR and PRF at the peptide level.

The BLAST algorithm emphasizes regions of local alignment to detect relationships among sequences which share only isolated regions of similarity (Altschul et al., 1990). Therefore, BLAST is not only used to calculate percent similarity between two sequences, but to locate regions of sequence similarity with a view to comparing structure and function. BLASTN is used to compare a nucleotide query sequence against a nucleotide sequence database. BLASTX is used to compare a nucleotide query sequence translated in all six reading frames against a protein sequence database. This option is used to find potential translation products of an unknown nucleotide sequence. TBLASTN is used to compare a protein query sequence against a nucleotide sequence database translated in all reading frames. BLASTP is used to compare an amino acid query sequence against a protein sequence database.

The *Arabidopsis* Information Resource (TAIR), at the *arabidopsis*.org website, is a collaborative effort between the Carnegie Institution of Washington, Department of Plant Biology, at Stanford University, and the National Center for Genome Resources (NCGR) at Santa Fe, N. Mex. TAIR provides genomic and literature data about *Arabidopsis thaliana* as well as links to the older AtDB database.

The Institute for Genomic Research (TIGR) is establishing a centralized database for *Arabidopsis* sequence annotation, available through the tigr.org/tdb/ath1/htmls/ath1.html website. The sequences in the TIGR database are submitted from all *Arabidopsis* Genome Initiative (AGI) labs, including TIGR (chromosome II), where they are analyzed and annotated. Tools at the TIGR ATH1 site allow the user to browse clones sorted by map positions on chromosome II and search the site by gene name, locus (in chromosome II) and sequence and to retrieve sequence segments. Users have FTP access to the entire genome sequence and predicted coding regions. The *Arabidopsis thaliana* Annotation Database (ATH1) will contain every sequence derived from *Arabidopsis* Genome Initiative (AGI) sequencing projects for the entire genome, annotated to a uniform standard, while both TAIR and TIGR use a variety of programs for sequence annotation.

Rouze et al., (*Curr. Opin. Plant Biol.* 2: 90-95, 1999) presents a review of the wide range of tools and resources available for gene structure analysis and states that approximately one-third of genes can be confidently assigned an identity or function based on nucleotide sequence homology, and up to another third can be assigned a putative identity based on regional or weak similarity.

Putative gene structure (especially the protein coding sequence) in a region of genomic DNA may be determined using the ORF Finder (Open Reading Frame Finder, available through NCBI), a graphical analysis tool which finds all open reading frames of a selectable minimum size in a sequence input by a user or in a sequence already in the database. ORF Finder identifies all open reading frames using the standard or alternative genetic codes and the deduced amino acid sequence can be saved in various formats and searched against the sequence database using the WWW BLAST server. The ORF Finder software may be downloaded as a stand alone program from the NCBI ftp site (ncbi.nlm.nih.gov/gorf/gorf.html).

Gene structure analysis programs may also be accessed through links at the TAIR site (at the *arabidopsis*.org/gene_id.html website) including GenScan, which facilitates the identification of complete gene structures in genomic DNA input into the program. The GeneFinder program, available as a link through TAIR or directly through the BCM GeneFinder site: http://dot.imgen.bcm.tmc.edu:9331/gene-finder/gf.html may be used to determine gene structure from a genomic sequence is. The GeneFinder program can search for putative intron splice sites, protein coding exons and promoter and poly-adenylation sites. GeneMark.hmm is a program useful for sequence annotation, and the analysis is tailored by species.

Links from major genome sequence information sites such as TAIR to other programs for finding ORFs, coding sequences, intron splice sites, translation start sites and terminator sequences in genomic nucleotide sequence include, but are not limited to: MZEFA, a software tool designed to predict putative internal protein coding exons in genomic DNA sequences; GRAIL, a software tool for analysis of the protein-coding potential of a DNA sequence, which is useful to identify terminal exons; NetPlantGene|NetGene2, which is useful or prediction of *Arabidopsis* splice sites from CBS; and NetStart, which is useful predictions of *Arabidopsis* translation starts from CBS.

In addition, once a DNA sequence and predicted amino acid sequence have been determined, various sequence motifs and structure/function predictions may be performed using e.g., .the Brutlag Bioinformatics Group "http://dna.Stanford.EDU", for predicting the biological function of genes and proteins from their primary sequence, predicting structures of proteins and DNA from sequence information, and understanding how and when genes are expressed; the ExPASy (Expert Protein Analysis System) proteomics server "http://www.expasy.ch/" of the Swiss Institute of Bioinformatics (SIB), which is dedicated to the analysis of protein sequences and structures and which provides an extensive list of links to protein databases and protein analysis tools:

VI. Confirmation And Analysis Of Candidate Genes

Analysis of Modified Gene Expression

Following identification of a candidate gene, further analysis is performed to determine whether expression of the gene has been modified by the insertional mutagen, generally by RNA analysis. Several techniques for analysis of mRNA, such as Northern blotting, slot blotting, ribonuclease protection, RT-PCR, quantitative RT-PCR, and microarray analysis are available and well known to skilled practitioners (e.g., Current Protocols in Molecular Biology (1994) Ausubel F M et al., eds., John Wiley & Sons, Inc., chapter 4; Baldwin D et al., Curr Opin Plant Biol. 2(2):96-103, 1999; Freeman W M et al., Biotechniques 26:112-125, 1999). The Taqman® system (Applied Biosystems, Foster City, Calif.; Gelmini S et al., Clinical Chemistry (1997) 43:752-758) is useful for quantitative RT-PCR analysis. In general, expression of the candidate gene is compared in transformant and wild type plants. A difference in the gene expression in transformant and wild type plants provides evidence that mutation of the candidate gene may be responsible for the mutant trait. If the insertional mutagen is predicted to cause a loss-of-function mutation (for instance, if the mutation appears recessive and/or if sequence analysis indicates that the insertional mutagen is inserted in regulatory or coding sequence of a candidate gene), the analysis must be done using plant tissue in which the candidate gene is normally expressed. Alternative methods include analysis of proteins and/or metabolites associated with an expressed candidate gene, for instance, by immunohistochemistry or enzymatic assay.

Analysis of Dominant or Recessive Inheritance Pattern

For candidate genes predicted to cause a mutant trait by mis-expression (i.e., via an enhancer element contained in the insertional mutagen), a further aspect of candidate gene analysis is confirmation of dominant expression pattern. In general, if a mutant trait is observed in the T1 generation, it is predicted to be dominant. Standard genetic analysis is used to confirm a dominant expression pattern, usually by production and analysis of F1 hybrids. Typically, F1 crosses are carried out by collecting pollen from T2 plants, which is used to pollinate wild type plants. Such crosses are carried out by taking at least approximately 4 flowers from each selected individual plants, typically using the T2 flower as the male pollen donor and flowers of the wild type plants as the female. 4-5 crosses are done for an individual of interest. Seed formed from crosses of the same individual are pooled, planted and grown to maturity as F1 hybrids. The generation of F1 hybrids exhibiting the mutant trait indicates that the mutant trait is dominant.

Mutant traits that are observed in T2 plants but not in T1 plants may be recessive. In general, a recessive mutant trait is observed in 25%, or fewer, of the T2 progeny of a T1 plant (i.e., the homozygous progeny).

Recapitulation of the Mutant Trait

For dominant mutations, further confirmation of a candidate gene's contribution to a mutant trait involves preparing a heterologous gene construct encoding the candidate gene, transforming wild-type plants with the construct, causing mis-expression of the candidate gene, and observing whether the transformed plants display the mutant trait. Wild-type plants that are transformed with this gene construct are termed "test plants." Sometimes, tissue explants (including plant cells) may be transformed instead of whole plants. Recapitulation of the mutant trait in progeny of the transformed test plant or explant provides strong evidence linking the candidate gene to the mutant trait. In general, each candidate gene that has been shown to be mis-expressed in transformant plants is tested in this manner.

The heterologous gene construct may be prepared in any manner expedient to effect its ultimate expression in the test plant or explant. Exemplary constructs comprise an *Agrobacterium* binary construct containing a selectable marker, and the candidate gene under control of a constitutive promoter. Numerous promoters useful for heterologous gene expression are available. Exemplary constitutive promoters include the raspberry E4 promoter (U.S. Pat. Nos. 5,783,393 and 5,783,394), the multimerized 35S CaMV (Jones J D et al, Transgenic Res 1:285-297 1992), the CsVMV promoter (Verdaguer B et al., Plant Mol Biol 37:1055-1067, 1998) and the melon actin promoter. Exemplary tissue-specific promoters include the tomato E4 and E8 promoters (U.S. Pat. No. 5,859,330) and the tomato 2AII gene promoter (Van Haaren M J J et al., Plant Mol Bio 21:625-640, 1993).

In general, a first recapitulation experiment involves transformation of test plants or explants of the same species as the originally transformed plant in which the mutant trait was identified. Recapitulation experiments may also transform test plants of different species. For instance, if a mutant trait is originally identified in *Arabidopsis*, the candidate gene may be mis-expressed in tomato and tobacco test plants.

When a candidate gene is predicted to cause the mutant trait by loss-of function mutation, independent confirmation of the association between the candidate gene and the mutant trait may involve inhibition of the endogenous candidate gene in wild type plants. Exemplary methods for practicing this aspect of the invention include, but are not limited to antisense suppression (Smith, et al., *Nature* 334:724-726, 1988); co-suppression (Napoli, et al, *Plant Cell* 2:279-289, 1989); ribozymes (PCT Publication WO 97/10328); and combinations of sense and antisense (Waterhouse, et al., *Proc. Natl. Acad. Sci. USA* 95:13959-13964, 1998).

Further Analysis

Standard molecular and genetic tests may be performed to further confirm the association between a candidate gene and an observed phenotype. A number of other techniques that are useful for determining (predicting or confirming) the function of a gene or gene product in plants are described below.

1. DNA/RNA analysis

DNA taken from a mutant plant may be sequenced to identify the mutation at the nucleotide level. The mutant phenotype may be rescued by overexpressing the wild type (WT) gene. The stage- and tissue-specific gene expression patterns in mutant vs. WT lines, for instance, by in situ hybridization, may be determined. Analysis of the methylation status of the gene, especially flanking regulatory regions, may be performed. Other suitable techniques include overexpression, ectopic expression, expression in other plant species and gene knock-out (reverse genetics, targeted knockout, viral induced gene silencing (VIGS, see Baulcombe D, *Arch Virol Suppl* 15:189-201, 1999).

In a preferred application, microarray analysis, also known as expression profiling or transcript profiling, is used to simultaneously measure differences or induced changes in the expression of many different genes. Techniques for microarray analysis are well known in the art (Schena M et al., Science (1995) 270:467-470; Baldwin D et al., 1999; Dangond F, Physiol Genomics (2000) 2:53-58; van Hal N L et al., J Biotechnol (2000) 78:271-280; Richmond T and Somerville S, Curr Opin Plant Biol (2000) 3:108-116). Microarray analysis of individual tagged lines may be carried out, especially those from which genes have been isolated. Such analysis can identify other genes that are coordinately regulated as a consequence of the overexpression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical or signaling pathway based on its overexpression phenotype or by sequence homology with related genes. Alternatively, analysis may comprise genetic crosses with WT lines and other mutant lines (creating double mutants) to order the gene in a pathway, or determining the effect of a mutation on expression of downstream "reporter" genes in a pathway.

4. Other Analyses

Other analyses may be performed to determine or confirm the participation of the isolated gene and its product in a particular metabolic or signaling pathway, and to help determine gene function.

In some cases, once a gene associated with an interesting phenotype has been isolated, characterized (i.e., sequenced), and its function confirmed, the sequence of the gene may be modified, for use in development of transgenic plants having desired phenotypes.

VII. Generation of an Indexed Library of Transformant Seeds

An important aspect of the invention is the generation of a collection (i.e., a library) of mutant seeds, transformed with the insertional mutagen, that may be stored and repeatedly accessed for different purposes, particularly for directed screens. In this aspect, the T2 seed is collected from T1 plants and is stored in indexed (e.g., bar coded) storage containers that identify the seed by plant identification number recorded in the electronic database. The seed library is stored under conditions that allow the long-term recovery of the seeds and generation of T2 plants therefrom. As used herein, "long-term" refers to a period of at least one year, preferably at least two years, more preferably at least five years, and more preferably at least ten years. Typical conditions for the long-term storage of seeds are a temperature of approximately 4° C. and low humidity. Each time seeds from the library are analyzed, e.g., in a screen, data regarding novel mutant traits observed in the transformed plant are recorded in the database and linked to the plant identification number.

In a preferred embodiment, production of T2 seed is repeated to the point where the seeds in the indexed library collectively represent a mutation in essentially every gene in the plant genome (i.e., "saturation of the genome"), preferably a mutation in at least 90% of genes in the genome, more preferably at least 95%, more preferably at least 99%. Using a collection of seeds which collectively represent saturation of the genome in a directed screen allow the evaluation of the contribution of every gene in the genome to the particular mutant trait.

Assessment of genome saturation will vary according to the plant. For plants with sequenced genomes, such as *Arabidopsis thaliana*, gene predictions can be done on a genome-wide scale. Comparison of the candidate genes with the gene prediction from the sequenced genome indicates degree of genome saturation. In the absence of a fully sequenced genome, other techniques can be used to predict genome saturation. In one aspect, sequences of candidate genes may be compared to a collection of expressed sequence tags (ESTs) to estimate genome saturation. Alternatively, estimation of genome size of the plant used, together with mapping information for the insertion sites and the presence of a physical and/or genetic map of the genome may be used. Since the preferred insertional mutagens show minimal bias towards particular chromosomes or genes, positions along a chromosome, or particular regions of genes, the sequence rescued from each insertion site can form the basis of a rough genomic map, and can indicate progress towards genome saturation.

VIII. System For Allowing Users To Associate Plant Phenotype And Genotype Information A. Network/Database Environment The system for functional gene discovery described herein requires that (1) phenotypic observations/measurements alone or together with nucleic acid sequence information be entered into a computer database, (2) that the information be searchable based on mutant traits and/or nucleic acid sequence ("plant records"); and (3) that the computer database interface with a computer network. Numerous commercial databases are available that can provide the platform for practicing this aspect of the invention, e.g., FILEMAKER PRO and Oracle databases.

Figure 3:
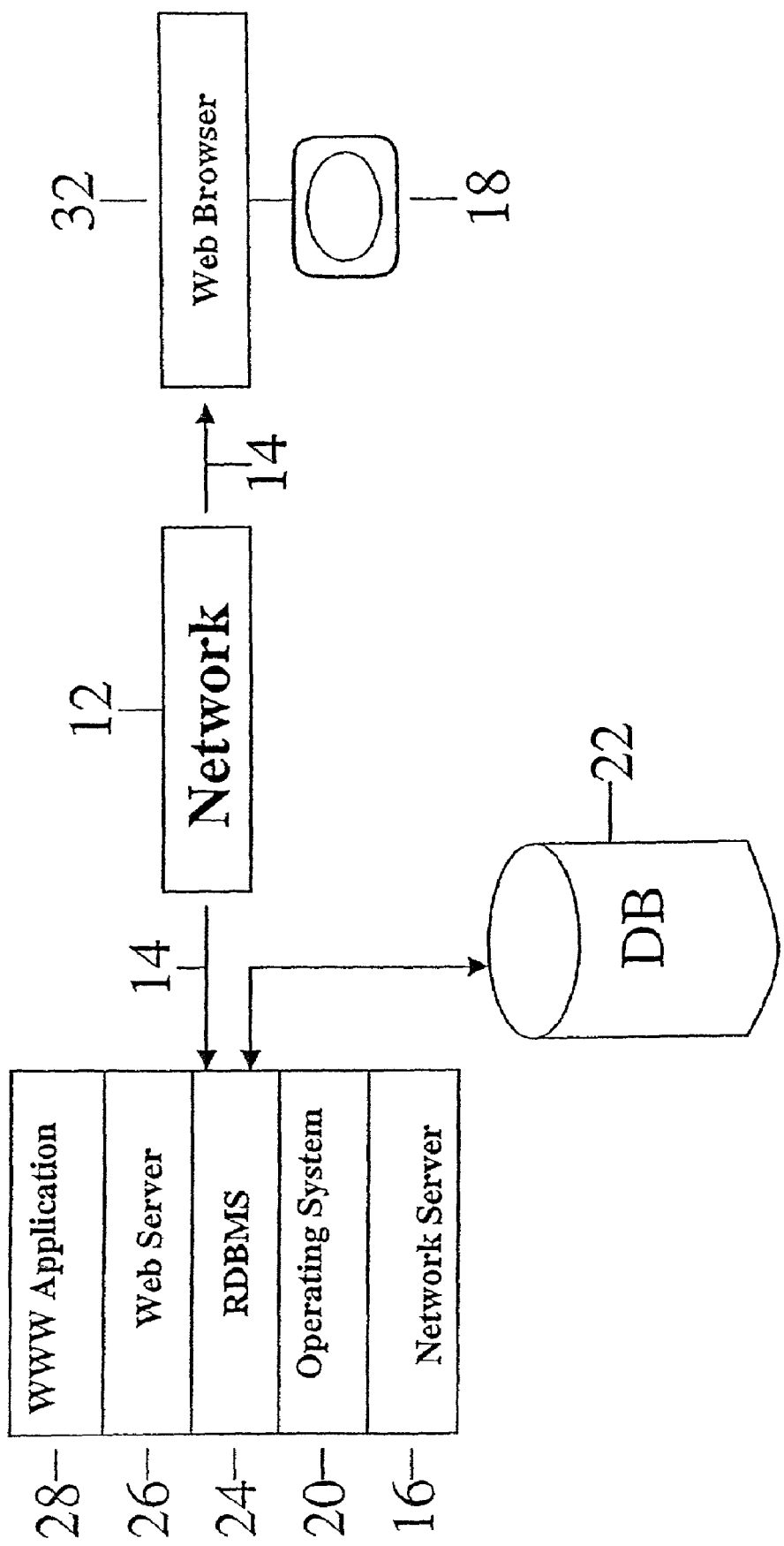
FIG. 3 is a schematic representation of a network that may be used for allowing users to access, retrieve and view information in a relational database containing the database of plant records, in accordance with one aspect of the present invention.

FIG. 3 is a schematic representation of a network 12 that may be used for allowing users to access, retrieve and view information in a relational database containing the database of plant records, in accordance with another aspect of the present invention. Network 12 includes a communication path 14 through which a network server 16 and a representative client 18 are connected. For ease of illustration, only a representative client is shown; however, it will be apparent to those skilled in the art that many more clients can also be connected. Network client 18 uses network 12 to access the database of plant records and associated resources provided by network server 16. The nature of the communication paths connecting network client 18 and network server 16 are not critical to the practice of the present invention. Such paths may be implemented as switched and/or non-switched paths using private and/or public facilities. Similarly, the topology of network 12 is not critical and may be implemented in a variety of ways including hierarchical and peer-to-peer networks. The network may be any one of a number of conventional network systems, including a local area network (LAN) or a wide area network (WAN) using Ethernet or the like. The network includes functionality for packaging client calls in a standard format (e.g., URL) together with any parameter information into a format suitable for transmission across communication path 14 for delivery to the server.

Network server 16 may be a hypermedia server, perhaps operating in conformity with the Hypertext Transfer Protocol (HTTP). The server includes hardware (see FIG. 3) and an operating system 20 necessary for running software for (i) accessing records in a plant database 22 in response to user requests, and (ii) presenting information to client computer 18. Such software may include, for example, a relational database management system 24 that runs on the operating system. The server also typically includes a World Wide Web server 26 and a World Wide Web application 28. World Wide Web application 28 includes executable code necessary for generation of database language statements (e.g., Standard Query Language (SQL) statements). Application 28 may also include a configuration file that contains pointers and addresses to the various software modules of the server, as well as to the database for servicing user requests.

Client computer 18 includes hardware and appropriate software to connect to a network and run a standard Web browser 32 which is used to access, view and interact with information provided by server 16. For example, client computer 18 may be any conventional networked computer, such as a PC, a Macintosh, or a Unix workstation running Netscape Navigator or Internet Explorer.

The hardware found in a typical computer, which may be used to implement a network server and/or network client, is well known in the art.

Database 22 is preferably arranged and configured to store the information contained on the plant records in relational format. Such a relational database supports a set of operations defined by relational algebra, and includes tables composed of rows and columns for the information. The database is relationally arranged so that a searched phenotypic trait can be associated with a plant having other phenotypic traits of interest or with a plant having a candidate gene sequence of interest, and so that a searched DNA sequence can be associated with a plant having phenotypic traits of interest.

B. Graphical User Interface (GUI)

Figure 4:
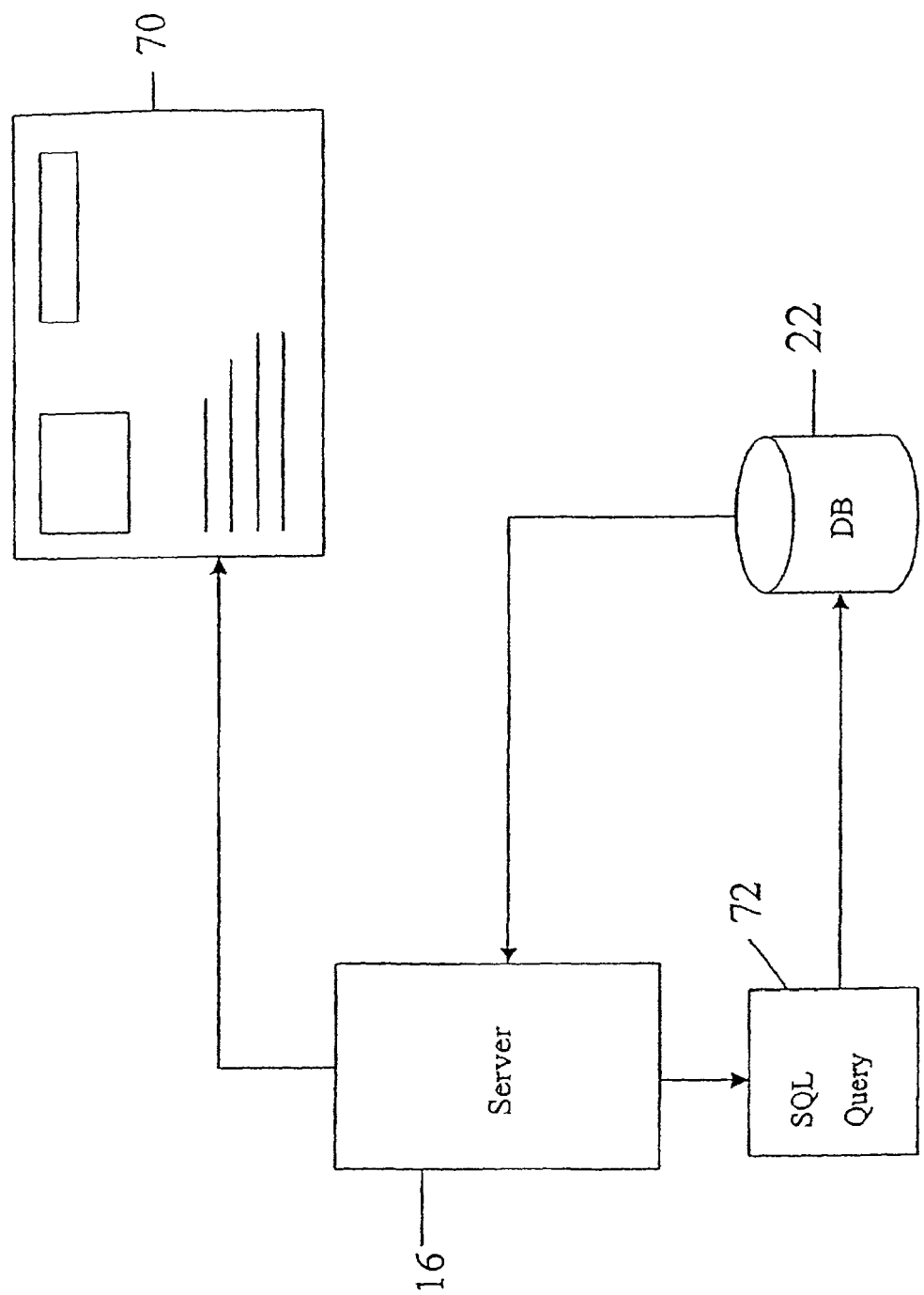
FIG. 4 is a schematic representation of an exemplary relationship between a graphical user interface 70 (GUI) which includes a plurality of screens (e.g., HTML pages) and a suite of functions for constructing and transmitting search requests, a server 16 where information is converted by the Web application component of the server to an SQL query 72 and selectively displaying data retrieved from the database 22.

Through Web browser 32 running on client 18 (FIG. 3), a user is presented with a graphical user interface (GUI) 70 (FIG. 4), which includes a plurality of screens (e.g., HTML pages) and a suite of functions for constructing and transmitting search requests, and selectively displaying data retrieved from database 22 (FIGS. 3, 4). The functions are preferably in the form of standard GUI elements, such as buttons, pull down menus, scroll bars, text boxes, etc. displayed on the screens. The GUI includes a main menu page from which various lines of inquiry can be followed. From the main menu, a user is able to navigate to a screen that includes a database search engine function. Such a screen includes a text box that is capable of receiving a user-specified search request, such as a mutant trait or DNA sequence, for searching the database. The search request is transmitted to server 16 and converted by the Web application component of the server to an SQL query 72. That query is then used by the relational database management system component of the server to search and extract relevant data from the database and provide that data to the server in an appropriate format. Server 16 then generates a new HTML page 70 displaying the retrieved information on the Web browser 32 running on client 18.

In one embodiment, the retrieved information is initially displayed as a hyper linked list individually identifying plant records retrieved from the database. The user then clicks on one of the hyperlink identifiers to display the information contained in a particular plant record in a new HTML page, which includes a plant image that is linked to the relevant data in the database. In one embodiment, such information includes plant identification number, an image or visual representation of the plant, a hyper linked list identifying additional phenotypic and/or genotypic information regarding the plant. For example, the list may link to biochemical and biological mutant trait information associated with the plant. For at least some records, the list further includes a candidate gene sequence link (i.e., to a candidate gene whose expression has been modified), indicating that the candidate gene sequence responsible for the searched trait is available, and may include a confirmation link indicating that the gene has been confirmed as responsible for the mutant trait. The user may click on any of these identifiers to obtain the corresponding information, which may be presented in a new HTML page or as a "pop-up" page, etc. When the user is finished viewing the information contained in one plant record, (s)he may easily navigate back to the original list of retrieved records, and click on another record to obtain information on that plant.

The GUI of the present invention is particularly advantageous in that it allows a user to easily associate a searched mutant trait with a plant having other mutant traits or with a plant having modified expression of a candidate gene sequence. It also allows a user to associate a searched DNA sequence with a plant having specific mutant traits.

C. Potential Business Arrangements

Upon selection of an interesting phenotype alone or in combination with an associated genotype, the user may select a potential business arrangement to be entered into with the provider regarding plant material or a plant gene sequence of interest, e.g., an assignment, a license or a joint venture.

In general, the type of business arrangement is based on the level of information available for a selected plant phenotype or a plant nucleic acid sequence, which is associated with a record or set of records in the database. In general, records listed to a database by the provider may be classified into three categories: (1) records associated with an identified mutant trait, (2) records associated with a mutant trait and nucleic acid sequence (i.e. an ORF) not yet confirmed by reintroduction into plants; and (3) records associated with a mutant trait and nucleic acid sequence (i.e., an ORF) where the relationship between the nucleic acid sequence and the mutant trait has been confirmed by reintroduction into plants.

It follows that the least amount of information is provided by the database in category (1), such that a lower royalty or other payment is typically associated with such records or sets of records, an intermediate royalty or other payment is associated with category (2) records or sets of records and the highest royalty or other payment is associated with category (3) records or sets of records.

Potential types of intellectual property ownership associated with records or sets of records that fall into category (1) include, ownership by the system user with or without a license to the provider or joint ownership by the provider and the user. Category (2) records or sets of records are typically associated with joint ownership by the provider and the system user or ownership by the provider with a license to the system user. The intellectual property associated with category (3) records or sets of records is typically owned by the provider, and may be licensed to one or more system users.

Such licenses may be exclusive, co-exclusive or non-exclusive, generally dependent upon which party contributes the most information. In general, when a system user derives sequence information associated with a particular phenotype of interest based on plant material supplied by the provider, the business relationship requires that once obtained, the nucleic acid sequence information be communicated to the provider for entry into a database.

IX. Applications of The System

From the foregoing, it can be appreciated that the methods of the present invention offer broad applicability to situations wherein it is desirable to identify a particular plant phenotype, alone or in combination with an associated gene sequence from a database of information derived from plants that have random genomic insertions of an insertional mutagen, with the goal of associating a particular phenotype or phenotypes with a genetic sequence. Of particular interest is the ability to search phenotypes based on a visual representation of the plant.

Large amounts of nucleic acid sequence information are being generated on a regular basis using advanced sequencing technology. The association of identified sequences with actual (not predicted) function and a demonstration of the connection between sequence information and biological function is proceeding at a much slower pace. The invention described herein provides a means to bridge the gap between such sequence information and the associated phenotypic traits of interest.

All publications, patents and patent applications are herein expressly incorporated by reference in their entirety.

While the invention has been described with reference to specific methods and embodiments, it will be appreciated that various modifications and changes may be made without departing from the invention.

The following examples illustrate, but in no way are intended to limit the present invention.

EXAMPLE 1

Functional Gene Discovery in *Arabidopsis*

An example of the use of the methods of the invention in *Arabidopsis* is described below. It will be understood that the method generally applies to all plants, however, details such as optimal plant growth conditions, transformation methods, selection conditions, are specific to the type of plant used in practicing the method.

Growth of *Arabidopsis thaliana* Plants.

General information on the care of *Arabidopsis* plants is found at the biosci.ohio-state.edu/~plantbio/Facilities/abrc/HANDLING.HTM website.

Briefly, *Arabidopsis* plants are grown in Premier HP soil which contains peat moss and perlite, using a minimal amount of N-P-K (171-2-133) fertilizer diluted to 1/10 the strength, with sub-irrigation, as needed and an 18 hr day length using natural light supplemented by high pressure sodium lamps at a temperature of 20-25° C. Seeds are sown under humidity domes for the first 4-7 days, then transferred to a greenhouse having approximately 70% humidity.

It will be appreciated that environmental factors affect morphology and are therefore taken into account when evaluating plants. Such factors include: fertilizer, temperature, day-length, light intensity, humidity, insect and fungal pathogens.

Plants begin flowering after about 3-4 weeks, with watering and fertilizing continued as needed until a majority of the siliques have turned yellow/brown. Then plants are left to dry out and seed collected by breaking open siliques to release the seed. Seed is stored at room temperature for a few days, then stored at 4° C. in an airtight container with desiccant.

Plants are monitored for pests and pathogens, particularly, fungus gnats, white flies, and aphids, with pest control applied as needed, e.g., application of Talstar and Azatin for whitefly, thrips and fungus gnats; application of Gnatrol for fungus gnats, biological control (e.g. mites, for gnat larvae) and safer soap.

*Arabidopsis* Transformation Protocol: ACTTAG

An *Agrobacterium* culture is prepared by starting a 50 ml culture 4-5 days prior to plant transformation (e.g., by "dunking"). Liquid cultures are grown at 28° C., on an orbital shaker at 200 rpm, in LBB with Carbenicillin (Cb) at 100 mg/l to select for the plasmid, with 50 mg/l Kanamycin (Kan) added to select for the helper plasmid. After 2 days, this small culture is used to inoculate 6-8 liters (L) of LBB with Cb 100 mg/l and Kan 50 mg/l, 1L each in 2000 ml Erlenmeyer flasks. Cultures are placed on a shaker for 2-3 days, checked for cell concentration by evaluating the $OD_{600}$ (visible light at 600 nm) using a spectrophotometer with an $OD_{600}$ reading for between 1.5-2.5 preferred. The cultures are then centrifuged at 4,500 RCF for 15 minutes at room temperature (18-22° C.), the bacteria resuspended to approximately $OD_{600}$=0.8 with about 500 ml needed per dunking vessel. Generally, 15-20 L is prepared for 200 pots, and 20-30 plants dunked at a time.

Healthy *Arabidopsis* plants are grown from wild type *Arabidopsis* seed, Ecotype: Col-0, until they flower, under long days (16 hrs) in pots in soil covered with bridal veil or window screen. Plants are dunked into the *Agrobacterium* culture (GV3101 with pMP90RK, helper plasmid) carrying ACT-TAG (binary plasmid PSKIO15) 2-3 days after clipping and a second time 5-8 days after the first, with no further trimming of the plants in between.

Above-ground parts of plant are dunked in *Agrobacterium* for 15 minutes, with gentle agitation, then placed on their sides, under a dome or cover for 16-24 hours to maintain high humidity, until the second dunking.

In one approach, transformants are selected with Finale (Basta, glufosinate ammonium, should be diluted at 1:1000 of an 11.33% solution). Seed is sprinkled in a flat (40 mg=2000 seed), cold treated for 2-3 days, and plants sprayed as soon as they germinate, with subsequent spraying a day or two apart, until transformants are easily selectable.

When the seedlings are eight to twelve days old, the majority are at the stage after the cotyledons have matured but before the primary leaves have developed. At this stage, the shoot tip is just starting to expand and push the cotyledons apart. In another approach, screening is initiated by four sprayings every other day, which thoroughly wet the seedlings with a solution of 1.0 g/L Kanamycin. During spraying, the number of germinated seedlings is noted for segregation analysis and percent germination data. Following sprayings, the non-transgenic seedlings produce chlorotic primary leaves and their hypocotyls dehydrate and collapse, killing the plant. Some of the transgenic seedlings show slight chlorotic spotting at the point of contact, where the Kanamycin was absorbed into the leaf, but their development continues unhindered. The survivors are counted and segregation data calculated after the non-transgenic plants have died (within two-three weeks following the sprayings). Survivors are transplanted into individual pots for further monitoring, then grown until they produced seed (T1), which is collected and sown to yield T1 plants.

In one example, plants transformed with constructs containing both the BAR and nptII selection cassettes have been successfully selected in soil by treatment with BASTA and kanamycin, respectively. In performing one exemplary selection, plants transformed with constructs containing either the CsVMV::nptII selection cassette or the RE4::nptII selection cassette were planted in soil and a solution of kanamycin in water was applied by either spraying the aerial portion of the plants daily or by watering the plants from the bottom. Spraying with a 500 microgram/ml kanamycin solution resulted in efficient selection with a minimum of false positives. In another exemplary application of the method, herbicide (BASTA) selection was carried out by spraying plants as soon as they germinated with Finale (B asta, glufosinate ammonium), diluted at 1:1000 of an 11.33% solution, followed by approximately 3 subsequent sprayings a day or two apart.

Following treatment with the selective agent, non-transgenic seedlings produced chlorotic primary leaves and their hypocotyls dehydrated and collapsed, killing the plant.

A fraction of the transformed plants, which survived the selection process, exhibited an interesting trait. T1 seed was stored (at 4° C. under desiccant), and bulk tissue collected from plants which exhibit a mutant trait.

T1 plants are grown until they produced seed (T2), which in some cases was collected and sown to yield T2 plants. T2 plants are treated in the same manner as T1 plants in that T2 plants are observed, observations are recorded (in notebooks and/or using a Palm Pilot, as further described herein) and photos are taken. Interesting T2 plants are also grown until they produce seed, seed is collected (T3) and sown to yield T3 plants. This cycle may be repeated multiple times until the interesting trait appears to be stable.

Morphological evaluation/Data Collection

Morphology assessments are made at several stages of plant development. T1 plants are observed at 4-5 weeks (vegetative stage), 6-7 weeks (flowering), and 8-9 weeks (fruiting). T2 pools of plants are observed weekly, with observations recorded after about week 4.

Observations are recorded using automated data collection means, e.g., a "Palm Pilot" which has a bar code scanner. Exemplary information for entry into a Palm Pilot includes plant flat (identified by a bar code and which contains 8 pools), pool information, date of planting for the flat; seed collection date, source and storage location of the seed (identified by plant ID/bar code) and when applicable, tissue collection date, type (either leaf or whole plant) and storage location.

Data synchronization may be accomplished by connecting a Palm Pilot to a computer using, e.g., the HotSync application on the Palm Pilot to download data into the computer. Photographs are taken using a digital camera (e.g., a Kodak DC 260 or 265 digital camera) to document images of all plants according to their pool location within a designated flat at 4-5 weeks after germination and to download images into the computer database, as well as to capture images of plants with a mutant trait at any stage.

In general, observations, measurements and the associated dates, tissue collections dates, seed collection dates, etc. are recorded and input into the database, such that individual plants may be identified and correlated with the various information that has been entered.

Seed Collection

Bulk seed is collected for future selection of transgenics from mature plants by rubbing mature siliques with fingers to release seed, using a sieve to remove chaff and pouring clean seed through a funnel into storage tubes to which are added desiccant, e.g., drierite chips.

T1 Selection/Evaluation

T1 plants are selected by applying an appropriate amount of seed to target 20-50 resistant plants per flat, after selection. For example, at a 1% transformation rate and a target of 2,500 T1 plants in total, one expects about 25 per flat (×100 flats=2500) when planting 100 μl of seed in each (100 μl=approximately 2,500 seed). Seeds are sprinkled over flats, put into cold storage for three days, then placed in a greenhouse.

Immediately following germination, all flats except the control are sprayed with a selective agent, e.g., a 1 ml/L solution of BASTA, Finale (11.33% glufosinate ammonium; final concentration=113 mg/L). Spraying is continued at 2-3 day intervals until resistant plants are easily selected from sensitive ones (usually after about 10 days). Three weeks after germination, surviving plants (those with true leaves and which are not chlorotic) are transplanted. In one approach, images of each group of plants (e.g., pool of each flat) are captured at four weeks, downloaded into the PhotoShop application on a computer, crop rotated and the images burned onto a compact disc, with a backup copy made for all images.

Tissue is collected tissue from each flat and labeled with the corresponding bar code and flat number. Tissue, e.g., leaf tissue is collected from each plant and stored on dry ice, then transferred to a −80° C. freezer.

Morphology Screen And Propagation of Plants With Mutant traits

In an exemplary application of the method, T1 seeds are planted in flats, the flats put in cold storage for three or four days and are then placed in a greenhouse or growth room for germination and growth. The resulting T1 plants are observed at regular intervals, e.g., weekly, with observations made in notebooks or recorded using a Palm Pilot, and images recorded such that observations and/or measurements are recorded in a database. A percentage of the "interesting" T1 lines showing morphological mutant traits are selected based upon observations made of the T1 plants. In the case that an interesting T1 plant is sterile, tissue is collected for DNA extraction and gene isolation. Otherwise, T2 seed is produced from the interesting line. T2 seed collected from T1 plants can be grown to produce T2 plants for observation, analysis and T3 seed production. T3 seed may then be used to produce T3 plants to confirm the mutant trait. DNA can then be extracted for use in gene isolation. It is also possible, after observing a mutant trait; to re-plant T2 seed from the collection for the production of T2 plants. The T2 plants can be used either as a source of tissue for DNA extraction and subsequent gene isolation or to make F1 hybrid seed when crossed with wild type plants. Crosses are carried out by taking 4 or 5 flowers from each of the selected individual plants, using T2 pollen as the male parent and wild type flowers as the female parent. The resulting F1 seed from each cross is pooled, planted and may be subjected to selection. Segregation is recorded and phenotype observed. F1 hybrid seed can then be used to produce F2 seed from which segregating F2 populations can be grown, segregation recorded and phenotype observed. These populations can also serve as a source of plant tissue for extraction of DNA and subsequent gene isolation activities.

Genomic DNA Extraction.

In general, Nucleon™ PhytoPure™ systems from Amersham™ is used for extracting genomic DNA. For example, 1.0 g of fresh plant tissue is ground in liquid nitrogen to yield a free flowing powder, then transferred to a 15 ml polypropylene centrifuge tube. 4.6 ml of Reagent 1 from the Nucleon™ PhytoPure™ kit was added with thorough mixing, followed by addition of 1.5 ml of Reagent 2 from the Nucleon™ PhytoPure™ kit, with inversion until a homogeneous mixture is obtained. The mixture is incubated at 65° C. in a shaking water bath for 10 minutes, and placed on ice for 20 minutes. The samples are removed from the ice, 2 ml of −20° C. chloroform added, mixed and centrifuged at 1300 g for 10 minutes. The supernatant is transferred into a fresh tube, 2 ml cold chloroform, 200 µl of Nucleon™ PhytoPure™ DNA extraction resin suspension added and the mixture shaken on a tilt shaker for 10 minutes at room temperature, then centrifuged at 1300 g for 10 minutes. Without disturbing the Nucleon resin suspension layer, the upper DNA containing phase is transferred into a fresh tube, centrifuged at 9500 rpm for 30 minutes to clarify the transferred aqueous phase if the upper phase appears cloudy, an equal volume of cold isopropanol added, and the tube is gently invert the tube until DNA precipitates and then it is pelleted by centrifugation, then washed with cold 70% ethanol, pelleted and air-dried.

DNA is resuspended in TE buffer (10 mM Tris. HCl, pH 7.4, 1 mM EDTA), containing RNase, incubated at 55° C. for 15 minutes, further extracted phenol/chloroform, then chloroform, run on a 1% agarose gel to check the DNA Quality, the DNA concentration determined by a DNA fluorometer (Hoeffer DyNA Quant 200).

Plasmid Rescue

Genomic DNA from single copy T-DNA insertion lines identified by Southern hybridization is digested by the restriction enzymes used in Southern Hybridization. The restriction fragments are then self-ligated and used to transform the E. Coli cells. The plasmids that contain a full-length pBluescript vector, 4×35S enhancer, and a right border T-DNA flanking genomic DNA fragment are rescued.

Genomic DNA is digested with a selected restriction enzyme under standard reaction conditions. Briefly, the restriction enzyme is heat inactivated at 65° C. for 20 minutes, phenol/chloroform and chloroform isoamyl (24:1) extracted once with each, then put into a ligation reaction containing the following:

| | |
|---|---|
| Digested Genomic DNA | 40 µl |
| 5X Ligation Buffer | 50 µl |
| Ligase (Gibcol, 1 U/µl) | 10 µl |
| ddH$_2$O | 150 µl |

The ligation reactions are left at 16° C. overnight, the ligated DNA is precipitated, resuspended in ddH$_2$O and used to transform E. coli SURE cells (Stratagene) via electroporation, with 10 pg of pUC18 plasmid as a control.

The transformation mixture is spread on two LB-plates containing 100 µg/ml ampicillin and incubated overnight at 37° C. Single colonies are picked from the pates and used to start a 5 ml LB-ampicillin broth culture of each overnight at 37° C. The plasmid is extracted from the culture and restriction digested to confirm the size of genomic insertion.

Sequencing of Rescued Plasmids

Sequencing may be conducted using an ABI Prism Big-Dye™ Terminator Cycle Sequencing Ready Reaction Kit (PE Applied Biosystem), AmpliTaq™ DNA Polymerase (Perkin-Elmer), an ABI Prism™ 310 Genetic Analyzer (Perkin-Elmer) and sequence analysis software, e.g., Sequencer™ 3.1.1 or MacVector 6.5.3, following the protocols from the manufacturer.

EXAMPLE 2

Description and Characterization of Activation Tagging Constructs

In one example, the Agrobacterium strain GV3101 containing the helper plasmid pMP90RK may be used to carry pSKI015, where the host and helper plasmid markers are kanamycin, gentamycin and rifampicin resistance.

In another example, pSKI074 (GenBank accession AF218466; Weigel D et al., 2000, supra), known to work in a similar context to pSKIO15, includes a selection cassette which contains the nptII structural gene conferring kanamycin resistance under the control of the Agrobacterium mannopine synthase promoter and terminator. Additional modifications to the selection cassette included construction of pAG3201, which has a selection cassette containing the nptII selection gene under the transcriptional control of the strong constitutive promoter CsVMV and the Agrobacterium gene 7 terminator, in place of the original mas pro-bar-ocs selection cassette; and pAG3202 which has a selection cassette containing the nptII selection gene under the transcriptional control of the moderate constitutive promoter RE4 and the Agrobacterium gene 7 terminator, in place of the existing mas pro-bar-ocs selection cassette.

In addition to these, pAG3205 has a selection cassette in which the nptII gene is under the control of a melon actin promoter containing a 5'UTR intron. The selection of the appropriate promoter for the selectable marker cassette will depend on the method of selection and the plant species. For example, the melon actin promoter may be an appropriate selection for rice transformation as the promoter has been shown to function as a strong constitutive promoter in monocots.

The activation tagging constructs designated pAG3201 and pAG3202 and pAG3205 were used to transform GV3-101/pMP90RK.

In a further example, the activation tagging construct pAG4201, composed of the pZPZ200 binary vector, the RE4-nptII-G7 selection cassette adjacent to the left T-DNA border, the pKS phagemid, and the 4×35S enhancer region adjacent to the right T-DNA border was transformed into both GV3101/pMP90RK and EHA101.

Transformed bacterial cell lines containing various activation tagging constructs were confirmed by selection on media containing the appropriate antibiotic. E. coli colonies and cultures were grown in selective media containing 100 micrograms/mil ampicillin. Agrobacterium colonies and cultures were grown in selective media containing 100 micrograms/ml carbenicillin. The presence of the pSKI015 construct was verified in colonies by PCR using primers that amplify the ocs terminator in the BAR selection cassette, a 35S enhancer sequence and a region of the pBluescript vector sequence. [PCR parameters were: 30 cycles:94° C. 30 seconds; 63° C. 40 seconds; 72° C. 120 seconds.]

A number of frozen cell stocks of lines carrying the activation tagging constructs have been generated. For long-term storage, PCR-positive colonies were grown in selective media, glycerol added to a final concentration of 30% and cultures quick frozen then stored at −80° C. For the initiation of dense Agrobacterium cultures for plant transformation, stock cultures were grown in selective media, glycerol added to a final concentration of 30%, and a number of 20 microliter aliquots quick frozen in liquid nitrogen and stored at −80° C.

In a routine analysis of activation tagged T1 *Arabidopsis* lines, all were confirmed as PCR positive for BAR. In an initial screen to survey activation tagged lines of *Arabidopsis* and to optimize amplification reaction conditions, genomic DNA was extracted from a sample of thirty-two activation tagged lines of *Arabidopsis*. The results of PCR amplification indicated that all lines were PCR-positive for the presence of the BAR selection cassette, and of the thirty-two lines PCR-screened for 35S enhancers, 30 lines (94%) had the ladder of four distinct products, indicating that all four copies of the 35S enhancer were present, while two lines had only three fragments, indicating the presence of an incomplete enhancer region.

EXAMPLE 3

Sequence Rescue from Tagged Lines by PCR

Using a pool of 8 activation tagged lines, genomic DNA was extracted for flanking sequence isolation.

In one example, TAIL-PCR (Thermal Asymmetric Interlaced; Liu et al. 1995. Plant Journal 8(3) 457-463) was carried out as described in Liu et al., 1995, including the sequence of the degenerate oligonucleotide primers. Sequence-specific oligonucleotide primers were also designed complimentary to the ocs terminator in the selection cassette and to the LB of the T-DNA of pSKI015, pAG3201 and pAG3202.

In another example, i-PCR (inverse PCR; Does et al., *Plant Molecular Biology* 17: 151-153, 1991) was carried out by using primers specific to T-DNA left and right borders. Briefly, genomic DNA was digested by different restriction enzymes and self-ligated, followed by one primary PCR reaction using the self-ligations and one nested PCR with the diluted primary PCR products. The nested PCR products were gel-purified and sequenced, and the genomic DNA sequence flanking left and right borders was identified by the BLAST analysis.

In another example, genomic DNA from a single copy T-DNA insertion line is digested by the restriction enzymes used in Southern Hybridization, the restriction fragments self-ligated and used to transform the E. coli cells. The plasmids that contain a full-length pBluescript vector, 4×35S enhancer, and a right border T-DNA flanking genomic DNA fragment are then rescued.

The ligated DNA is precipitated, resuspended in ddH$_2$O and used to transform E. coli SURE cells (Stratagene) via electroporation, with 10 pg of pUC18 plasmid as a control.

The transformation mixture is spread on two LB-plates containing 100 µg/ml ampicillin and incubated overnight at 37° C. Single colonies are picked from the plates and used to start a 5 ml LB-ampicillin broth culture from each colony by culturing overnight at 37° C. The plasmid is also extracted from the culture and restriction digested to confirm the size of genomic insertion.

EXAMPLE 4

Fungal, Bacterial, Viral and Insect Resistance Testing.

An exemplary screen for bacterial resistance is carried out by growing healthy plants from T2 seed and wild type untransformed control seed, under long days (16 hrs) in pots in soil covered with bridal veil or window screen.

In an exemplary application of the methods using *Arabidopsis*, clear plastic domes are placed over flats of plants which are stored at 4° C. for 3 days to vernalize the seed. After 3 days, the flats are removed and placed in the greenhouse or growth chamber, under the following plant growth environmental conditions: short day length (10 hr light) with 120 uE/cm$^{-2}$ light intensity and cool temperatures (25° C. day/20° C. night)-conditions in order to promote vegetative growth. Wild type (e.g., *Arabidopsis* Col-0) plants serve as susceptible control plants for the bacterial screen. In one exemplary approach, one wild type plant is planted for every 8 ACTTAG T2 plants that are transplanted (e.g., 2 flats of 144 wild type seedlings per 16 flats of transformed seedlings; such that 128 T2 lines is equal to 1024 ACTTAG seedlings). In this exemplary embodiment, one flat of wild type plant Col-0 plants is sprayed with inoculum (positive control), and the other with Mock inoculum (negative control).

ACTTAG T2 plants are sprayed with a selective agent, e.g., BASTA (Finale) 3 times at 2 to 3 day intervals, the plants are grown for an additional time under the environmental conditions set forth above, them grown under "dew room" conditions (>95% relative humidity, 40 to 60 uE/cm$^{-2}$, short day length (10 hr light) for 24 hr prior to inoculation.

In general, bacterial inoculum are prepared from −80° C. stocks of bacterial isolates stored in 50% glycerol, using virulent and avirulent strains of the particular pathogen (e.g. *Pseudomonas syringae* pv. *maculicola* M4 (vir) strain and *Pseudomonas syringae* pv. *maculicola* avrRpml strain). Glycerol stocks are removed from the −80° C. freezer, streaked onto selective media plates with rifampicin (100 mg/L) using a sterile inoculation loop, then incubated for 3 days at 28° C. These starter cultures are used to inoculate larger liquid cultures for use in inoculating plants. The OD$_{600nm}$ of 1 mL of each overnight culture is measured, with cultures that reach OD 0.5-0.8 units (mid-log phase actively growing culture) used for scale-up of inoculum. Once scaled-up inocula are diluted as appropriate to obtain 10$^8$ bacterial colony forming units (cfu) per 1 ml.

Mock inoculations are carried out by drenching the leaf surface of the entire rosette of each plant on a wild type plant flat (negative controls). Bacterial inoculations and incubation are carried out by drenching the leaf surface for the entire rosette of ACTTAG T2 and wild type plants with a given inoculum diluted as set forth above.

In general, plants are scored for bacterial disease resistance at 24 hrs post-inoculation, by evaluation of bacterial disease symptoms. There is a "phenotypic window" separating a resistance and a susceptible interaction. The goal of the resistance screen is to identify those individuals that display a resistance phenotype (relatively soon after infection) as opposed to a diseased (susceptible) phenotype which occurs later in the disease cycle. It will be understood that the ability to distinguish between these phenotypes is different for each pathogen/plant combination being tested.

Typically, the interaction between a plant pathogenic bacteria and the resistant plant occurs relatively quickly (16-28 hrs post-inoculation, "hpi"). This is why it is critical to evaluate the plant relatively soon after inoculation (24 hrs). Leaves on the resistant plant display what is known as a hypersensitive response ("HR"). At 24 hpi a small lesion forms on the inoculated leaf surface formed by collapse of the cells immediately surrounding the bacterial entry site. The resistant (or incompatible) condition is maintained throughout the subsequent 7 day evaluation period. The HR is tightly limited to the necrotic lesion which completely dries out and has sharp border between the green healthy tissue and the necrotic lesion. There is no chlorosis beyond the margin of the necrotic lesion.

The resistant (incompatible) and the susceptible (compatible) interaction phenotypes differ in two respects: (1) timing of appearance of symptoms and (2) the type of symptoms displayed. Whereas the resistant plants display a restricted necrosis (HR) surrounding the inoculation point at 24 hpi, no symptoms are visible in the susceptible plants at this time. The compatible interaction (susceptible) phenotype begins to appear at around 72 hpi. It is characterized by water-soaked chlorotic margins surrounding a dry necrotic tissue. Over the course of the 7 day evaluation period, these lesions continue to enlarge at the chlorotic margins and become necrotic in the middle.

T2 ACTTAG and wild type plants are observed in a growth room at 24 hours post-inoculation and plants visually identified that display a hypersensitive response, with the HR symptoms comparable to the symptoms displayed on the avirulent bacteria-inoculated wild type plants. Susceptible plants do not show any symptoms at this time. Observations are recorded using a Palm Pilot hand held scanner.

Resistant plants are flagged and putative resistant plants monitored during the course of the evaluation period to verify that the HR condition is maintained.

The observation steps are repeated at approximately 48 and 72 hrs post-inoculation, with observations performed in the growth room where the plants are being maintained. Flags are removed from flats if disease symptoms appear in a previously flagged T2 plant. The wild type plants that have been inoculated with a virulent pathogen (positive controls) are used as a visual reference standard for identifying disease symptoms.

At 72 hrs (3 days) post-inoculation, all flats are moved to a greenhouse to continue incubating the inoculated plants. T2 lines which were earlier identified as putative resistant lines are observed further and if the HR condition is maintained over the entire 7 day course of evaluation (i.e. the resistance phenotype (dry tightly limited necrotic lesions) is still displayed at 7 days post-inoculation), the T2 line is scored as resistant. Again observations are recorded using a Palm Pilot hand held scanner and the 8 individuals from a T2 line scored as resistant photographed using a Kodak DC265 camera. In addition, tissue is harvested from putative disease resistant plants which are grown in the greenhouse under long day conditions to promote flowering of the plants with seed collected as further described above. Plants that pass this initial resistance test are re-screened using a disease resistance confirmatory test, are further analyzed by gene isolation and identification and are crossed to wild type plants for subsequent rescreen of F2 plants.

It will be appreciated that the details of a given bacterial screen may vary dependent upon the bacteria/plant combination being tested and this example serves as a general description of such a bacterial screen. Additional examples of such a bacterial screen are generally known in the art.

EXAMPLE 5

Stress Resistance Screens

Directed screens are described that are performed in order to identify genes involved in resistance to stress. The screens are described for in *Arabidopsis*, but may also be performed in other plants using similar methods. All screens use plants transformed with the activation tagging vector pSKIO15, using standard transformation procedures, as described above. For all screens, it is important that plants receive the same care and that all treatments, insect outbreaks, temperature fluctuations, etc. be recorded.

Drought Resistance Screen

A T2 screen for drought resistance is performed.

Flats are prepared with 18 pots per flat; 6 transformant lines are planted into each flat, 3 pots each. Wild type Col0 seed for controls is also prepared. Seed is suspended in agar and pipetted into each pot. Wetted and covered flats are placed in growth rooms (typically 23-25° C., 40% humidity, 18 h light 6 h dark). Domes are left on for 4-7 days (until seed has germinated). Domes are removed and the total number of plants germinated per line is counted and recorded using a Palm Pilot. Plants are then sprayed with Basta until susceptible lines are easily identified. The number of resistant plants per line is recorded using a Palm Pilot. Watering, and applications of fertilizer, gnatrol etc. are carefully recorded and indicate where the treatment of one pot, line, or flat might differ from the rest. Temperature, light, and humidity are also recorded in a Palm Pilot. The plants are cared for as evenly as possible across flats and experiments. At the time when plants have a healthy rosette, but have not yet bolted (3-4 weeks old), watering ceases (half of the wild type controls receive normal watering). Plants are evaluated for interesting morphologies at the time watering is stopped.

After about 15 days, or when the "no water" wild type plants are noticeably wilted, lines are evaluated for drought tolerance, and tolerant lines are marked. One leaf from each plant in marked lines is collected, and leaves from each line are pooled in 2 ml cryo-vials, which are labeled and placed in −80° C. freezer. Two leaves from each plant in marked lines are then collected, and leaves from each line are pooled in 50 ml falcon tube, which are barcode labeled. These pooled leaves ("samples") are weighed on an analytical balance; for each line, the line ID and this "fresh weight" (FW) are recorded in the Palm Pilot. Samples are replaced in 50 ml tubes, 25 ml DI water is added to each tube, and the tubes are placed at 5° C. After 18-24 hours, tubes are removed from the cold. Each leaf is carefully removed from the water and gently blotted to dry its surface. Samples are weighed, and weights are recorded as "turgid weight" (TW). Samples are placed into aluminum weighing dishes and put into a 70-80° C. incubator. After 7 days, samples are re-weighed, and weights are recorded as "dry weight" (DW). The relative water content (RWC) is calculated using the formula: RWC=(FW−DW)/(TW−DW)×100.

Plants are recovered from drought conditions. Once drought tolerance is assessed, plants are left to dry out until all of the lines' (except drought tolerant lines) rosette leaves have turned purple-brown. All lines are then watered. After 3-5 days, recovery is evaluated. This is determined by presence of new growth, recovery of leaf color in older leaves, and may utilize RWC or other analyses. Lines showing no variation from wild type, in either general morphology or drought tolerance/recovery, will not be followed, and will be discarded after this analysis.

Following recovery, interesting lines are marked for seed collection and re-screening. Seeds from marked lines are collected either individually or as a T3 seed pool. In general, for lines showing interesting phenotypes, tissue is harvested and seed collected from individuals or pooled siblings in a line. Where T3 seed is not available, T2 seed is recovered. Seed from each line of interest is planted alongside wild type seed. The drought resistance screen is repeated as described above for re-screening.

Salt Tolerance Screen

A salt tolerance screen is performed to identify and isolate gene(s) that confer salt (NaCl) tolerance in *Arabidopsis*. It has been determined experimentally that NaCl at concentrations greater than 250 mM completely abolish expansion and green pigmentation of wild-type cotyledons in *Arabidopsis*.

A primary screen is conducted with T1 plants, using a germination assay. T1 seed is plated evenly in media supplemented with 250 mM NaCl. For negative and positive controls, wild type (Col-O) seed is plated in plates with and without, respectively, the supplemental NaCl. Plates are incubated for two days at 4° C., then transferred to a growth room and incubated an additional 7 to 14 days.

It is expected that a range of phenotypes, of varying intensities, will be observed in the germination assay. Salt tolerant germination is classified in five stages: 1) imbibation, emergence of radicle; 2) expansion and greening of cotyledons; 3) elongation of the hypocotyl; 4) elongation of the root and formation of root hairs; 5) development of true leaves. A high stringency screen requires seedlings to progress through all five stages, which will select activation tagged mutants with the most robust phenotypes. In the event that such mutants are not observed, low stringency criteria are used. For a low stringency screen, not all of the criteria will need to be met; for example, expanded cotyledons will be scored as a positive, regardless of root elongation.

Any putative positives (i.e., salt resistant plants) are transferred to soil and kept in the growth room. At approximately 3 weeks, leaf samples are collected for PCR detection of the activation tagging vector. Plants are grown to maturity, and T2 seed collected.

A secondary screen is conducted with T2 plants. From each individual selected as a positive from the primary screen, approximately 40 T2 seed are plated in 250 mM NaCl. Salt tolerance is scored, as is the segregation ratio of tolerance.

Copper Tolerance Screen

A screen for copper tolerance was developed in order to identify and isolate gene(s) whose altered expression confers copper tolerance and allows normal plant growth and development in the presence of an inhibitory level of copper. It has been experimentally determined that the lowest completely inhibitory concentration (LCI) of copper is 160 µM for hypocotyl and cotyledon expansion and the development of true leaves in wild type (Col-0) *Arabidopsis*. Root elongation is inhibited at 100 µM, and negative gravitropism of the hypocotyl is completely inhibited at 50 µM $CuSO_4$.

For the primary screen, pooled T2 lines are plated on media supplemented with 160 µM $CuSO_4$. Controls include wild type (Col-0 cand Shadara) plants germinating on plates with no copper and copper at the Col-0 LCI for germination. Plates are incubated 3 days at 4° C., then transferred to the growth room and incubated an additional 10 days.

Copper sensitivity is evaluated with germination assays, which are performed as described above for salt resistance screens.

Any putative positives (i.e., copper resistant plants) are transferred to soil and kept in growth room. At approximately 3 weeks, leaf samples are collected for PCR detection of the activation tagging vector. Plants are grown to maturity and T3 seed collected.

A secondary screen is conducted with T3 plants.

As one example of utility, the gene(s) isolated from this screen will be developed for use as a plant selectable marker for crop improvement.

The invention claimed is:

1. A method for multigenerational plant trait analysis and associated data management comprising:
    a) generating a random insertion of an insertional mutagen in the genome of a T0 plant, and collecting T1 seed from said T0 plant, wherein said insertional mutagen is capable of a loss of function and a gain of function mutation;
    b) growing T1 plants from the seed collected in (a) under conditions to select transformed T1 plants, and assigning a T1 identification number to each transformed T1 plant selected;
    c) analyzing a transformed T1 plant grown in (b) for dominant mutant traits and recording at least one dominant mutant trait observed in the transformed T1 plant, wherein a record of a dominant mutant trait observed in a transformed T1 plant is linked to the T1 identification number assigned to the T1 plant analyzed;
    d) collecting T2 seed from T1 plants analyzed in (c), and assigning a T2 identification number to said seed, wherein the T2 identification number is linked to the T1 identification number assigned to the T1 plant analyzed in (c);
    e) growing T2 plants from the T2 seed collected in (d); and
    f) analyzing a T2 plant grown in (e) for recessive mutant traits and recording at least one recessive mutant trait observed in the analyzed T2 plant that was not present in its parent T1 plant, wherein a record is generated that associates the information of the analyzed T2 plant to any information recorded about its parent T1 plant.

2. The method of claim 1 wherein the insertional mutagen is an activation tagging vector.

3. The method of claim 2 wherein the activation tagging vector comprises an enhancer selected from the group consisting of a multimerized CaMV 35S enhancer, a figwort mosaic virus enhancer, a peanut chlorotic streak caulimovirus enhancer, and a mirabilis mosaic virus enhancer.

4. The method of claim 3 wherein the enhancer is a mirabilis mosaic virus enhancer.

5. The method of claim 1 wherein the T0 plant is selected from the group consisting of *Arabidopsis*, corn, tomato, and rice.

6. The method of claim 1 wherein the insertion mutagen encodes a selectable marker selected from the group consisting of an antibiotic resistance gene and an herbicide resistance gene.

7. The method of claim 1 wherein in step (b), prior to assigning T1 identification numbers to transformed plants, transformed plants are transplanted into perimeter wells of a multiwell container comprising a central well in which a barcode is provided, wherein a single perimeter well contains a single T1 plant, and wherein the T1 identification number assigned to each T1 plant in a perimeter well derives from the barcode in the corresponding central well and the relative position of the perimeter well holding said T1 plant.

8. The method of claim 1 wherein the T2 plants are analyzed by performing a directed screen to identify altered resistance to an herbicide.

9. The method of claim 1 wherein the T2 plants are analyzed by performing a directed screen to identify altered resistance to a pathogen, said pathogen selected from the group consisting of fungus, bacteria, virus, nematode, and insect.

10. The method of claim 1 wherein the T2 plants are analyzed by performing a directed screen to identify altered stress tolerance, said stress selected from the group consisting of drought, salt, and metal.

11. The method of claim 1 wherein the T2 plants are analyzed by performing a directed screen to identify altered level of a biochemical component, said biochemical component selected from the group consisting of vitamins, minerals, amino acids, carbohydrates, lipids, oils, nitrogenous bases, isoprenoids, phenylpropanoids, and alkaloids.

12. The method of claim 1 wherein the mutant traits observed in (c) and (f) are recorded using a predefined vocabulary.

13. The method of claim 1 wherein the T2 seed collected in (d) is distributed into a plurality of storage containers and stored under conditions that allow long-term recovery of the seeds and generation of T2 plants therefrom.

14. The method of claim 13 wherein each of said storage containers is barcoded to relate the T2 seed contained therein with the corresponding T2 identification number.

15. The method of claim 1 additionally comprising:
(g) reviewing the data for the mutant trait recorded in step (c) and/or step (f);
(h) obtaining T2 seed collected in (d) which is associated with the specific mutant trait queried in (g);
(i) performing a directed screen on the T2 seed obtained in (h) or on plants grown therefrom; and
(j) recording the results of the targeted screen such that the targeted screen results entry is linked to the T2 identification number assigned to the T2 seed.

16. The method of claim 15 wherein the specific mutant trait is a morphological trait.

17. The method of claim 13 wherein steps (a) through (f) are repeated such that essentially every gene in the genome of the plant being analyzed is mutated by an insertional mutagen and a library of seeds that collectively represent saturation of the plant genome with insertional mutagens that generate mutant traits is generated and contained within the storage containers.

18. The method of claim 17 wherein the T0 plant is *Arabidopsis*.

19. The method of claim 1 wherein a candidate gene responsible for the mutant trait recorded in step (c) or step (f) is identified by additional steps comprising:

(g) rescuing DNA flanking the insertional mutagen from a T1 or subsequent generation transformed plant;
(h) identifying at least one candidate gene from the DNA rescued in (g); and
(i) identifying a candidate gene identified in (h) that is over-expressed in the transformed plant.

20. The method of claim 19 wherein the insertional mutagen comprises an enhancer element and wherein the mutant trait is recorded in step (c) or step (f), wherein confirmation that the candidate gene identified in (i) causes the mutant trait is achieved by additional steps comprising:
(j) preparing a heterologous gene construct that encodes the candidate gene identified in (i) under control of a heterologous enhancer element capable of effecting mis-expression of said candidate gene;
(k) generating a transformed test plant or explant thereof that is the same species as the T0 plant in (a) with the heterologous gene construct;
(l) generating transformed progeny from the transformed test plant or explant thereof generated in (k) that mis-express the candidate gene; and
(m) identifying transformed progeny generated in (l) that display the mutant trait.

21. The method of claim 20 further comprising:
(n) transforming a test plant or explant thereof that is a different species than the T0 plant in (a) with said heterologous gene construct;
(o) generating transformed progeny from the transformed test plant or explant thereof generated in (n) that mis-express the candidate gene; and
(p) identifying transformed progeny generated in (o) that display one of the specific mutant traits.

22. A method for multigenerational plant trait analysis and associated data management comprising:
a) generating a random insertion of an insertional mutagen in the genome of a T0 plant, and collecting T1 seed from said T0 plant, wherein said insertional mutagen is capable of a loss of function and a gain of function mutation;
b) growing T1 plants from the seed collected in (a) under conditions to select transformed T1 plants, and assigning a T1 identification number to each transformed T1 plant selected;
c) analyzing a transformed T1 plant grown in (b) for dominant mutant traits and recording at least one dominant mutant trait observed in the transformed T1 plant, wherein a record of a dominant mutant trait observed in a transformed T1 plant is linked to the T1 identification number assigned to the T1 plant analyzed, wherein the mutant trait is a morphological phenotype;
d) collecting T2 seed from T1 plants analyzed in (c), and assigning a T2 identification number to said seed, wherein the T2 identification number is linked to the T1 identification number assigned to the T1 plant analyzed in (c);
e) growing T2 plants from the T2 seed collected in (d); and
f) analyzing a T2 plant grown in (e) for recessive mutant traits and recording at least one recessive mutant trait observed in the analyzed T2 plant that was not present in its parent T1 plant, wherein a record is generated that associates the information of the analyzed T2 plant to any information recorded about its parent T1 plant, and wherein the mutant trait is a morphological phenotype.

* * * * *